United States Patent
Levin et al.

(10) Patent No.: US 9,731,136 B2
(45) Date of Patent: Aug. 15, 2017

(54) METHODS AND APPARATUS TO STIMULATE THE HEART

(71) Applicant: BackBeat Medical, Inc., New Hope, PA (US)

(72) Inventors: Howard Levin, Teaneck, NJ (US); Mark Gelfand, New York, NY (US)

(73) Assignee: BackBeat Medical, Inc., New Hope, PA (US)

( * ) Notice: Subject to any disclaimer, the term of this patent is extended or adjusted under 35 U.S.C. 154(b) by 0 days.

(21) Appl. No.: 15/163,078

(22) Filed: May 24, 2016

(65) Prior Publication Data
US 2016/0263383 A1 Sep. 15, 2016

Related U.S. Application Data

(63) Continuation of application No. 13/688,978, filed on Nov. 29, 2012, now Pat. No. 9,370,661, which is a continuation of application No. 12/555,389, filed on Sep. 8, 2009, now Pat. No. 8,340,763.

(60) Provisional application No. 61/095,120, filed on Sep. 8, 2008.

(51) Int. Cl.
| | | |
|---|---|---|
| *A61N 1/362* | (2006.01) | |
| *A61N 1/365* | (2006.01) | |
| *A61N 1/36* | (2006.01) | |
| *A61N 1/368* | (2006.01) | |

(52) U.S. Cl.
CPC ......... *A61N 1/36542* (2013.01); *A61N 1/368* (2013.01); *A61N 1/3621* (2013.01); *A61N 1/3627* (2013.01); *A61N 1/3684* (2013.01); *A61N 1/36117* (2013.01); *A61N 1/36564* (2013.01)

(58) Field of Classification Search
CPC ... A61B 5/0452; A61N 1/3624; A61N 1/3684
USPC .................................................. 607/9, 17, 19
See application file for complete search history.

(56) References Cited

U.S. PATENT DOCUMENTS

| | | | |
|---|---|---|---|
| 3,683,934 | A | 8/1972 | Bukowiecki et al. |
| 3,939,844 | A | 2/1976 | Pequignot |
| 4,712,555 | A | 12/1987 | Thornander et al. |
| 5,213,098 | A | 5/1993 | Bennett et al. |
| 5,601,613 | A | 2/1997 | Florio et al. |

(Continued)

FOREIGN PATENT DOCUMENTS

| | | |
|---|---|---|
| CN | 1662278 A | 8/2005 |
| CN | 106029165 A | 10/2016 |

(Continued)

OTHER PUBLICATIONS

Notice of Allowance issued Jan. 18, 2017 in U.S. Appl. No. 15/143,742.

(Continued)

*Primary Examiner* — Carl H Layno
*Assistant Examiner* — Jon Eric C Morales
(74) *Attorney, Agent, or Firm* — Plumsea Law Group, LLC

(57) ABSTRACT

A method and apparatus for treatment of hypertension and heart failure by increasing secretion of endogenous atrial hormones by pacing of the heart. Pacing is done during the ventricular refractory period resulting in premature atrial contraction that does not result in ventricular contraction. Pacing results in the atrial wall stress, peripheral vasodilation, ANP secretion. Concomitant reduction of the heart rate is monitored and controlled as needed with backup pacing.

18 Claims, 10 Drawing Sheets

(56) References Cited

U.S. PATENT DOCUMENTS

| | | | |
|---|---|---|---|
| 5,928,271 | A | 7/1999 | Hess et al. |
| 6,377,852 | B1 | 4/2002 | Bornzin et al. |
| 6,507,756 | B1 | 1/2003 | Heynen et al. |
| 6,668,195 | B2 | 12/2003 | Warman et al. |
| 6,701,187 | B1 | 3/2004 | Bornzin et al. |
| 7,096,064 | B2 | 8/2006 | Deno et al. |
| 7,184,832 | B2 | 2/2007 | Deno et al. |
| 7,233,824 | B2 | 6/2007 | Kleckner et al. |
| 7,286,873 | B2 | 10/2007 | Havel et al. |
| 7,289,849 | B2 | 10/2007 | Baynham |
| 7,363,077 | B1 | 4/2008 | Min et al. |
| 7,674,222 | B2 | 3/2010 | Nikolic et al. |
| 7,869,874 | B2 | 1/2011 | Levin et al. |
| 8,165,674 | B2 | 4/2012 | Levin et al. |
| 8,187,160 | B2 | 5/2012 | Criscione et al. |
| 8,340,763 | B2 | 12/2012 | Levin et al. |
| 8,515,536 | B2 | 8/2013 | Levin et al. |
| 8,521,280 | B2 | 8/2013 | Levin et al. |
| 9,008,769 | B2 | 4/2015 | Mika et al. |
| 9,333,352 | B2 | 5/2016 | Mika et al. |
| 9,370,661 | B2 | 6/2016 | Levin et al. |
| 9,370,662 | B2 | 6/2016 | Mika et al. |
| 9,427,586 | B2 | 8/2016 | Levin et al. |
| 9,526,900 | B2 | 12/2016 | Mika et al. |
| 9,656,086 | B2 | 5/2017 | Mika et al. |
| 2004/0049235 | A1 | 3/2004 | Deno et al. |
| 2004/0138715 | A1 | 7/2004 | Van Groeningen et al. |
| 2004/0186523 | A1 | 9/2004 | Florio |
| 2004/0215268 | A1 | 10/2004 | Corbucci |
| 2005/0038478 | A1 | 2/2005 | Klepfer et al. |
| 2005/0075676 | A1 | 4/2005 | Deno et al. |
| 2005/0090872 | A1 | 4/2005 | Deno et al. |
| 2005/0101998 | A1 | 5/2005 | Kleckner et al. |
| 2005/0149131 | A1 | 7/2005 | Libbus et al. |
| 2006/0173502 | A1 | 8/2006 | Baynham |
| 2007/0073352 | A1 | 3/2007 | Euler et al. |
| 2007/0299477 | A1 | 12/2007 | Kleckner et al. |
| 2008/0027488 | A1 | 1/2008 | Coles et al. |
| 2008/0077187 | A1 | 3/2008 | Levin et al. |
| 2008/0109043 | A1 | 5/2008 | Salo et al. |
| 2009/0018608 | A1 | 1/2009 | Schwartz et al. |
| 2010/0094370 | A1 | 4/2010 | Levin et al. |
| 2010/0204741 | A1 | 8/2010 | Tweden et al. |
| 2011/0160787 | A1 | 6/2011 | Greenhut et al. |
| 2011/0172731 | A1 | 7/2011 | Levin et al. |
| 2012/0109237 | A1 | 5/2012 | Xiao et al. |
| 2012/0215272 | A1 | 8/2012 | Levin et al. |
| 2014/0180353 | A1 | 6/2014 | Mika et al. |
| 2016/0243368 | A1 | 8/2016 | Mika et al. |
| 2016/0339244 | A1 | 11/2016 | Levin et al. |
| 2017/0072203 | A1 | 3/2017 | Mika et al. |
| 2017/0080235 | A1 | 3/2017 | Mika et al. |

FOREIGN PATENT DOCUMENTS

| | | |
|---|---|---|
| JP | 2016-540589 A | 12/2016 |
| WO | 2007021258 | 2/2007 |
| WO | 2017044794 | 3/2017 |

OTHER PUBLICATIONS

Amendment filed Jan. 19, 2017 in U.S. Appl. No. 13/960,015.
Notice of Allowance mailed Feb. 22, 2017 in U.S. Appl. No. 13/960,015.
Notice of Intention to Grant issued Jan. 3, 2017 in European Patent Application No. 13826807.3.
Response to Office Action filed Jan. 19, 2017 in Chinese Patent Application No. 201380072479.3, and English translation thereof.
Lopez et al., "Reducing Heart Rate of the Dog by Electrical Stimulation", pp. 414-429, vol. 15 (Circ. Res. 1964).
Lister et al., "The Hemodynamic Effect of Slowing the Heart Rate by Paired or Coupled Stimulation of the Atria", pp. 362-368 (Am. Heart J. Mar. 1967).
Braunwald et al., "Editorial: Paired Electrical Stimulation of the Heart: A Physiologic Riddle and a Clinical Challenge," pp. 677-681, vol. 32, No. 5 (Circulation Nov. 1965).
Arbel et al., "Successful Treatment of Drug-Resistant Atrial Tachycardia and Intractable Congestive Heart Failure with Permanent Coupled Atrial Pacing," pp. 336-340, vol. 41 (Am. J. or Cardiology Feb. 1978).
"Information Manual, Model 5837 R-Wave Coupled Pulse Generator", 20 pages, Prelim. Ed. III, Medtronic (Jul. 1965).
Siddons et al., Cardiac Pacemakers, pp. 200-217, Pub. No. 680 of American Lecture Series (1968, Charles Thomas Publisher).
Schooderwoerd et al., "Atrial Natriuretic Peptides During Experimental Atrial Tachycardia: Role of Developing Tachycardiomyopathy," pp. 927-932, vol. 15, No. 8 (J. of Cardiovascular Electrophysiology Aug. 2004).
Nishimura, Kazunobu et al., "Atrial pacing stimulates secretion of atrial natriuretic polypeptide without elevation of atrial pressure in awake dogs with experimental complete atrioventricular block." Circ. Res. 1990;66;115-122.
Willems, Rik M.D. et al., "Different Patterns of Angiotensin II and Atrial Natriuretic Peptide Secretion in a Sheep Model of Atrial Fibrillation." Journal of Cardiovascular Electrophysiology. 2001;12.12;1387-1392.
Zupan, Igor et al. "Effects of Systolic Atrial Function on Plasma Renin Activity and Natriuretic Peptide Secretion after—High Rate Atrial and Ventricular Pacing in Dogs." Pace. 2005;28.Supp 1;S270-S274.
Calderone, Angelino "The Therapeutic Effect of Natriuretic Peptides in Heart Failure; Differential Regulation of Endothelial and Inducible Nitric Oxide Synthases" Heart Failure Reviews, 2003;8;55-70.
Han, Bo et al., "Cardiovascular Effects of Natriuretic Peptides and Their Interrelation with Endothelin-1" Cardiovascular Drugs and Therapy, 2003;17;41-42.
PCT Invitation to Pay Additional Fees mailed Oct. 17, 2014 in International Application No. PCT/US2014/042777.
PCT Notification of Transmittal of the International Search Report and the Written Opinion of the International Searching Authority; International Search Report; and Written Opinion, mailed Jan. 2, 2015 in International Application No. PCT/US2014/042777.
PCT Notification of Transmittal of the International Search Report and the Written Opinion of the International Searching Authority; Declaration of Non-Establishment of International Search Report; and PCT Written Opinion of International Searching Authority, mailed Apr. 24, 2014 in International Application No. PCT/US2013/076600.
Notice of Allowance mailed Dec. 16, 2014 in U.S. Appl. No. 13/826,215.
Office Action mailed Jun. 4, 2015 in U.S. Appl. No. 13/957,499.
Office Action mailed Jun. 10, 2015 in U.S. Appl. No. 13/960,015.
Office Action mailed Jul. 13, 2015 in U.S. Appl. No. 14/642,952.
Amendment filed Oct. 9, 2015 in U.S. Appl. No. 14/642,952.
Office Action mailed Nov. 4, 2015 in U.S. Appl. No. 14/427,478.
Amendment filed Nov. 30, 2015 in U.S. Appl. No. 13/957,499.
Amendment filed Dec. 3, 2015 in U.S. Appl. No. 13/960,015.
Notice of Allowance mailed Jan. 8, 2016 in U.S. Appl. No. 14/642,952.
Amendment filed Jan. 13, 2016 in U.S. Appl. No. 14/427,478.
Final Office Action mailed Jan. 20, 2016 in U.S. Appl. No. 13/960,015.
Notice of Allowance mailed Feb. 12, 2016 in U.S. Appl. No. 14/427,478.
Office Action mailed Mar. 4, 2016 in U.S. Appl. No. 14/667,931.
Amendment filed Apr. 7, 2016 in U.S. Appl. No. 13/960,015.
Notice of Allowance mailed Apr. 13, 2016 in U.S. Appl. No. 13/957,499.
Advisory Action mailed Apr. 18, 2016 in U.S. Appl. No. 13/960,015.
Office Action mailed May 27, 2016 in European Patent Application No. 13826807.3.
Amendment filed Jun. 6, 2016 in U.S. Appl. No. 13/960,015.
Notice of Allowance issued Aug. 17, 2016 in U.S. Appl. No. 14/667,931.

(56) References Cited

OTHER PUBLICATIONS

Amendment filed Sep. 27, 2016 in U.S. Appl. No. 15/143,742.
PCT Notification of Transmittal of the International Search Report and the Written Opinion of the International Searching Authority; International Search Report; and Written Opinion, mailed Nov. 28, 2016 in International Application No. PCT/US2016/051023.
Office Action mailed Jun. 28, 2016 in U.S. Appl. No. 15/143,742.
Office Action mailed Jul. 21, 2016 in U.S. Appl. No. 13/960,015.
Amendment filed Jul. 25, 2016 in U.S. Appl. No. 14/667,931.
Office Action issued Sep. 5, 2016 in Chinese Patent Application No. 201380072479.3, and English translation thereof.
Response to Office Action filed Sep. 27, 2016 in European Patent Application No. 13826807.3.
Office Action dated Mar. 24, 2017 in U.S. Appl. No. 15/372,603.
Decision to Grant dated May 26, 2017 in European Patent Application No. 13826807.3.

Figure 4
Atrial Pacing
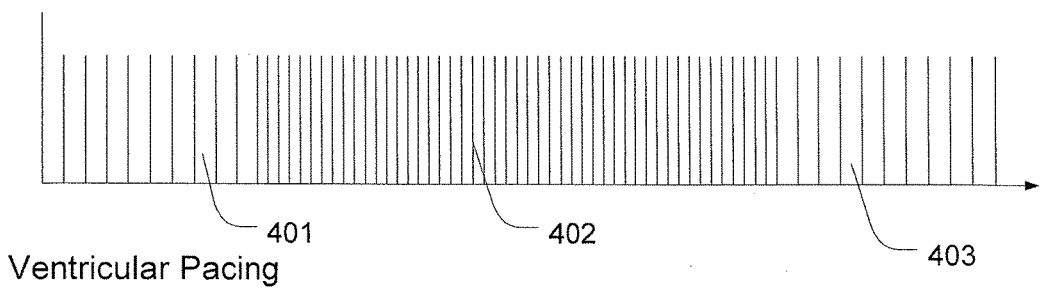
Ventricular Pacing
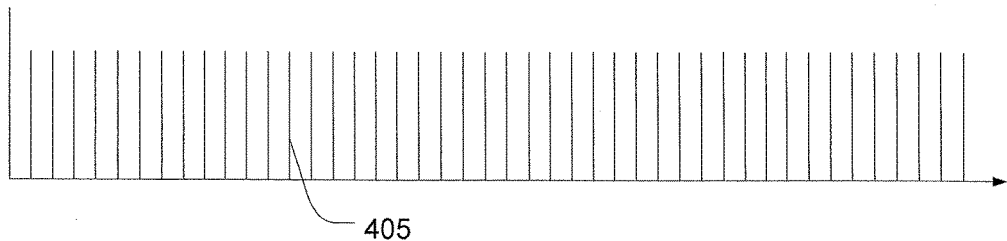

METHODS AND APPARATUS TO STIMULATE THE HEART

RELATED APPLICATIONS

This application is a continuation of U.S. application Ser. No. 13/688,978, filed Nov. 29, 2012, now U.S. Pat. No. 9,370,661, issued Jun. 21, 2016, which is a continuation of U.S. application Ser. No. 12/555,389, filed Sep. 8, 2009, now U.S. Pat. No. 8,340,763, issued Dec. 25, 2012, which claims priority to U.S. Provisional Patent Application No. 61/095,120, filed Sep. 8, 2008, all of which are herein incorporated by reference in their entirety.

BACKGROUND

Implantable devices for cardiac stimulation and pacing therapy are disclosed for cardiac therapies involving the controlled delivery of electrical stimulations to the heart for the treatment of hypertension, congestive heart failure, and an apparatus for delivering such therapies with the objective of increasing stress of atrial muscle walls, altering sympathetic and parasympathetic nerve stimulation and causing secretion of hormones such as Atrial Natriuretic Peptide (ANP) by the heart muscle and to cause vasodilatation of blood vessels.

Congestive Heart Failure

Congestive heart failure (CHF) occurs when muscle cells in the heart die or no longer function properly, causing the heart to lose its ability to pump enough blood through the body. Heart failure usually develops gradually, over many years, as the heart becomes less and less efficient. It can be mild, scarcely affecting an individual's life, or severe, making even simple activities difficult.

Congestive heart failure (CHF) accounts for over 1 million hospital admissions yearly in the United States (U.S.) and is associated with a 5-year mortality rate of 40%-50%. In the U.S., CHF is currently the most costly cardiovascular disease, with the total estimated direct and indirect costs approaching $56 billion in 1999.

Recent advances in the treatment of CHF with medications, including angiotensin-converting enzyme (ACE) inhibitors, beta-blockers (Carvedilol, Bisoprolol, Metoprolol), Hydralazine with nitrates, and Spironolactone have resulted in significantly improved survival rates. Although many medications have been clinically beneficial, they fall short of clinician's expectations and as a result consideration has turned to procedures and devices as additional and more potent heart failure therapy.

There has been recent enthusiasm for biventricular pacing (pacing both pumping chambers of the heart) in congestive heart failure patients. It is estimated that 30% to 50% of patients with CHF have inter-ventricular conduction defects. These conduction defects lead to a discoordinated contraction of the left and right ventricles of an already failing and inefficient heart. When the right ventricle alone is paced with a pacemaker, the delayed activation of the left ventricle, can also lead to significant dyssynchrony (delay) in left ventricular contraction and relaxation.

Because ventricular arrhythmias continue to threaten CHF patients and many anti-arrhythmic drugs have unacceptable side effects, a sophisticated implantable cardioverter-defibrillator (ICD) device has shown encouraging results. Biventricular pacing in combination with ICDs demonstrates a trend toward improved survival. Preliminary data in animals and humans using subthreshold (of the type that does not by itself cause heart muscle to contract) stimulation of the heart muscle to modulate cardiac contractility are encouraging and may further enhance the quality of life of CHF patients.

Many patients with CHF are not candidates for biventricular pacing or do not respond to this treatment strategy. This also applies to other recent advances and experimental therapies. There is a long felt need for new and better CHF therapies that will improve and prolong the life of heart failure patients and reduce the burden on the medical system. These new therapies should preferably not require a major surgery, prolonged stay in the hospital or frequent visits to the doctor's office.

Hypertension

It is generally accepted that high blood pressure (HBP, also called hypertension) is bad, but most people don't know why, and what the term really means. In fact, all humans have high blood pressure some of the time, and would not be able to function if without periodic hypertension, such as during exercise. High blood pressure is of concern when it persists for long periods of time or is extremely high over a very short (hours) period of time. The adverse effects of HBP usually take many years to develop. But, clinically important HBP is common. According to official government figures, 50 million people in the United States suffer from unhealthy HBP.

While everyone has high blood pressure some of the time, many people live their entire lives with moderately high blood pressure and never know it until it is notice on a routine visit to the doctor. Unfortunately, not all people are so lucky. In these people, high blood pressure significantly increases the risk of a number of serious events, mainly strokes and heart attacks.

More specifically, the damage caused by high blood pressure is of three general sorts. The first is the one everyone thinks of—bursting a blood vessel. While this is dramatic and disastrous when it happens, it's actually the least common of the three problems. It occurs most frequently in the blood vessels of the brain, where the smaller arteries may develop a weak spot, called an aneurysm. This is an area where the wall is thinner than normal and a bulge develops. When there is a sudden surge of pressure the aneurysm may burst, resulting in bleeding into the tissues. If this occurs in the brain, it is a stroke. In contrast, if an aneurysm occurs in the aorta (the main blood vessel in the body is a ruptured aortic aneurysm. Both of these events can lead to permanent damage and death.

The second adverse consequence of high blood pressure is that it accelerates the deposition of cholesterol in the arteries forming a blockage. This problem takes many years to develop and it is difficult to detect, at least until it causes a major blockage. The most important sites in the human body to be affected by cholesterol blockage are the heart, where the blockage can cause angina and heart attacks; the brain, where it causes strokes; the kidneys, where it causes renal failure (and can also make the blood pressure go even higher); and the legs, where it causes a condition known as intermittent claudication, which means pain during walking and may even lead to losing a limb.

Third, high blood pressure puts a strain on the heart. Because it has to work harder than normal to pump blood against a higher pressure, the heart muscle enlarges, just as any other muscle does when it is used excessively.

Over a long period of time, high blood pressure can lead to congestive heart failure, the most frequent cause for hospitalization in the United States. When the blood pressure reaches a certain high pressure level for a sufficient length of time it sets off a vicious cycle of damage to the heart, brain, and kidneys, resulting in further elevation of the pressure.

Classification of hypertension by its severity is somewhat arbitrary because there is no precise level of blood pressure above which it suddenly becomes dangerous. Historically, blood pressure has been primarily classified according to diastolic pressure. Someone whose diastolic pressure runs between 90 and 95 mm Hg may be regarded as having borderline hypertension, and diastolic pressure between 95 and 110 mm Hg is considered moderate, and at higher levels diastolic pressure is severe.

Recent data suggests that the systolic pressure is as effective as, and maybe more effective than, diastolic blood pressure in determining the patient's risk for serious adverse events. Systolic hypertension is mainly seen in people over the age of 65 and is characterized by a high systolic, but normal diastolic, pressure (a reading of 170/80 mm Hg would be typical). Systolic hypertension is typically caused by an age-related loss of elasticity of the major arteries.

Another form of HBP is referred to as Labile hypertension, which is a commonly used term for describing people whose blood pressure is unusually labile or variable. The most dangerous type of HBP is malignant hypertension or high blood pressure with evidence on physical exam that this pressure is causing an acute deleterious affecting on vital organ function. Malignant hypertension is regarded as an emergency requiring immediate treatment in a hospital. If untreated, malignant hypertension can be rapidly fatal. Although more people are treated with drugs nowadays than before, malignant hypertension is still common.

The objective of HBP treatment is not simply to lower the blood pressure, but to prevent its consequences, such as strokes and heart attacks. According to the American Heart Association high blood pressure is present in 50,000,000 Americans (Defined as systolic pressure 140 mm Hg or greater, and/or diastolic pressure 90 mm Hg or greater, or taking antihypertensive medication). Of those with HBP, 31.6 percent are unaware they have it; 27.4 percent are on medication and have it controlled; 26.2 percent are on medication but don't have their HBP under control; and 14.8 percent aren't on medication. In most cases, high blood pressure can be controlled with one or a combination of oral drugs. Of those patients that take medication to control HBP, many suffer from debilitating side effects of these drugs such as heart arrhythmias, inability to exercise or do normal activities of daily living and impotence.

Electric Activity of the Heart

In a given cardiac cycle (corresponding to one "beat" of the heart), the two atria contract to force the blood therein into the ventricles. A short time later, the two ventricles contract, forcing the blood therein to the lungs (from the right ventricle) or through the body (from the left ventricle). Meanwhile, blood from the body refills the right atrium and blood from the lungs refills the left atrium, waiting for the next cycle to begin. A healthy adult human heart may beat at a rate of 60-80 beats per minute (bpm) while at rest, and may increase its rate to 140-180 bpm when the adult is engaging in strenuous physical exercise, or undergoing other physiologic stress.

The healthy heart controls its rhythm from its sinoatrial (SA) node, located in the upper portion of the right atrium. The SA node generates an electrical impulse at a rate commonly referred to as the "sinus" or "intrinsic" rate. This impulse is delivered from the SA node to the atrial tissue when the atria are intended to contract. The electrical signal continues to propagate from the atrial tissue through the atrioventricular (AV) node, a specialized collection of tissue that serves as a "gatekeeper" for the impulses traveling between the atria and the ventricles. After a suitable delay (on the order of 140-220 milliseconds), the signal finally propagates to the ventricular tissue and the ventricles are stimulated to contract. SA node is the natural pacemaker of the heart. If it is disabled, there are other specialized areas of the heart muscle that can generate an intrinsic heart rate.

The ventricular muscle tissue in the heart is much more massive than the atrial muscle tissue. The atrial muscle tissue need only produce a contraction sufficient to move the blood a very short distance from the respective atrium to its corresponding ventricle. The ventricular muscle tissue, on the other hand, must produce a contraction sufficient to push the blood through the complete circulatory system of the entire body. Even though total loss of atrial contraction can lead to a small reduction of cardiac output it is not an immediate risk to life. Conversely, the atria of the heart can sustain a higher number of contractions per minute than the ventricles without endangering life.

Electronic Cardiac Pacemakers

An electronic pacemaker (pacemaker) provides electrical stimulation pulses to the appropriate chamber(s) of the heart (atrium, ventricle, or both) in the event the heart is unable to beat on its own, e.g., in the event either the SA node fails to generate its own natural stimulation pulses at an appropriate sinus rate or in the event such natural stimulation pulses do not effectively propagate to the appropriate cardiac tissue. Most modern pacemakers accomplish this function by operating in a "demand" mode where stimulation pulses from the pacemaker are provided to the heart only when it is not beating on its own, as sensed by monitoring the appropriate chamber of the heart for the occurrence of a P-wave or an R-wave. If a P-wave or an R-wave is not sensed by the pacemaker within a prescribed period of time (which period of time is often referred to as the "escape interval"), then a stimulation pulse is generated at the conclusion of this prescribed period of time and delivered to the appropriate heart chamber via a pacemaker lead. Pacemaker leads are isolated wires (called leads) equipped with sensing and stimulating electrodes.

Modern programmable pacemakers are generally of two types: (1) single-chamber pacemakers, and (2) dual-chamber pacemakers. In a single-chamber pacemaker, the pacemaker provides stimulation pulses to, and senses cardiac activity within, a single-chamber of the heart (e.g., either the right ventricle or the right atrium). In a dual-chamber pacemaker, the pacemaker provides stimulation pulses to, and senses cardiac activity within, two chambers of the heart, e.g., both the right atrium and the right ventricle. The left atrium and left ventricle of the heart can also be paced, provided that suitable electrical contacts are made therewith.

Much has been written and described about the various types of pacemakers and the advantages and disadvantages of each. For example, U.S. Pat. No. 4,712,555 of Thornander et al. and U.S. Pat. No. 5,601,613 of Florio et al. present background information about pacemakers and the manner in which they interface with a patient's heart.

One of the most versatile programmable pacemakers available today is the DDDR pacemaker. This pacemaker represents a fully automatic pacemaker which is capable of sensing and pacing in both the atrium and the ventricle, and is also capable of adjusting the pacing rate based on one or more physiological factors, such as the patient's activity level. It is commonly accepted that the DDDR pacemaker is superior in that it can maintain AV synchrony while providing bradycardia (slow heart beat) support. It is also generally more expensive than other, simpler types of pacemakers. A description of DDDR pacing is included in this disclosure as a state of the art.

In general, DDDR pacing has four functional states: (1) P-wave sensing, ventricular pacing (PV); (2) atrial pacing, ventricular pacing (AV); (3) P-wave sensing, R-wave sensing (PR); and (4) atrial pacing, R-wave sensing (AR).

It is accepted as important and advantageous, for the patient with complete or partial heart block, that the PV state of the DDDR pacemaker tracks the atrial rate, which is set by the heart's SA node, and then paces in the ventricle at a rate that follows this atrial rate. It is assumed that because the rate set by the SA node represents the rate at which the heart should beat in order to meet the physiologic demands of the body (at least for a heart having a properly functioning SA node) the rate maintained in the ventricle by such a pacemaker is truly physiologic.

In some instances, a given patient may develop dangerously fast atrial rhythms, which result from a pathologic arrhythmia such as a pathological tachycardia, fibrillation, or flutter. In these cases, a DDDR pacemaker may pace the ventricle in response to the sensed atrial arrhythmia up to a programmed maximum tracking rate (MTR). The MTR defines the upper limit for the ventricular rate when the pacemaker is tracking the intrinsic atrial rate. As a result, the MTR sets the limit above which the ventricles cannot be paced, regardless of the intrinsic atrial rate. Thus, the purpose of the MTR is to prevent rapid ventricular stimulation, which could occur if the intrinsic atrial rate becomes very high and the pacemaker attempts to track atrial activity with 1:1 AV synchrony.

When the intrinsic atrial rate exceeds the MTR the pacemaker may initiate one or more upper atrial rate response functions—such as automatically switching the pacemaker's mode of operation from an atrial tracking mode to a non-atrial rate tracking mode.

The heart's natural response to a very high atrial rate involves a natural phenomenon known as "blocking"—where the AV node attempts to maintain a form of AV synchrony by "dropping out" occasional ventricular beats when the high atrial rate exceeds a certain natural threshold i.e., the refractory period of the heart tissue. The blocking phenomenon is often expressed as a ratio of the atrial beats to the ventricular beats (e.g. 6:5, 4:3, etc.). Of particular importance is a 2:1 block condition where there are two atrial beats for every one ventricular beat. The 2:1 block condition is a natural response to a very high atrial rate, during which full ventricular rate synchronization (i.e. at a 1:1 ratio) would be dangerous to the patient.

Some known pacemakers emulate this 2:1 condition, by tracking P-waves up to the device's programmed total refractory period (TARP) of the heart. That is, P-waves which fall in the total refractory period are not tracked, and the device is said to have a "2:1 response mode." During the 2:1 block response mode, the ventricles are paced at a lower rate than the natural atrial rate, because P-waves occurring soon after ventricular events are ignored for the purposes of calculating the ventricular pacing rate. As a result, the 2:1 block response mode prevents the pacemaker from pacing the ventricles at a tachycardia rate.

The 2:1 block response mode is an effective response for dealing with short incidences of high atrial rates and in preventing occurrence of a pacemaker mediated tachycardia resulting from retrograde P-waves. However, the 2:1 block response mode may become uncomfortable for the patient if it is maintained for an extended period of time due to programmed long atrial refractory periods, because the pacing rate will be ½ of the required physiologic rate.

Many more advanced pacemaker operation modes have been described and sometimes implemented. Some of these modes included sensing abnormally high atrial rates and prevented them from causing rapid ventricular rates. Common to prior pacing no attempt has been made to induce a rapid (faster than normal) atrial rate by pacing or to pace atria at rate higher than ventricles.

Pacemaker Syndrome

Although pacemakers provide relief from life-threatening arrhythmias and can improve quality of life significantly, they also can function in a nonphysiologic manner, which is accompanied by nontrivial morbidity. Pacemakers functioning in the VVI mode (e.g., a pacing mode in which the native atrial electrical or contractile states are not sensed and ignored by the pacemaker) have been noted to sacrifice the atrial contribution to ventricular output. In some instances, and because of this lack of feedback, the timing of native atrial contraction and pacemaker-induced ventricular contraction is such that the atrial contraction occurs during ventricular contraction or against closed atrio-ventricular (A-V) valves (Tricuspid and Mitral), producing reverse blood flow and nonphysiologic pressure waves. The A-V valves normally open passively whenever the pressure in the atrium exceeds the pressure in the ventricle. The pressure in the ventricles is low during ventricular diastole (or ventricular filling period). In the case of non-physiological pacing, the A-V vales are not able to be normally opened by the pressure in the atrium during atrial contraction as the ventricles are in their pumping period (called ventricular systole) and the pressure in the ventricles significantly exceeds the maximum possible pressure able to be generated in the atrial muscle contraction. This abnormal, non-physiological relationship of atrial to ventricular contraction can occur in other pacing modes if a patient's heart tissue is susceptible to allowing abnormal retrograde (e.g., from the ventricle to the atria) conduction of native or pacemaker-induced ventricular electrical activity.

Pacemaker syndrome was first described as a collection of symptoms associated with right ventricular pacing. Since its first discovery, there have been many definitions of pacemaker syndrome, and the understanding of the cause of pacemaker syndrome is still under investigation. In a general sense, pacemaker syndrome can be defined as the symptoms associated with right ventricular pacing relieved with the return of A-V synchrony. Recently, most authors have recognized that pacemaker syndrome, which initially was described in patients with ventricular pacemakers, is related to nonphysiologic timing of atrial and ventricular contractions, which may occur in a variety of pacing modes. Some have proposed renaming the syndrome "A-V dyssynchrony syndrome," which more specifically reflects the mechanism responsible for symptom production.

The symptoms of pacemaker syndrome included dyspnea (shortness of breath) and even syncope (fainting). Syncope is temporary loss of consciousness and posture, described as "fainting" or "passing out." It's usually related to temporary insufficient blood flow to the brain. It's a common problem, accounting for 3 percent of emergency room visits and 6 percent of hospital admissions. It most often occurs when 1) the blood pressure is too low (hypotension) and/or 2) the heart doesn't pump a normal supply of blood to the brain.

In pacemaker syndrome patients, syncope occurs secondary to retrograde, ventricular to atrial (V-A) conduction resulting in the contraction of the atria against closed A-V valves. One effect of the elevated atrial and venous pressures associated with the contraction against closed A-V valves is to cause a vagal afferent response resulting in peripheral vasodilatation leading to a marked lowering of blood pressure (termed hypotension). Syncope is usually associated with systolic blood pressure declines of greater than 20 mm Hg that can occur with the onset of pacing.

Pacemaker syndrome can also lead to decreased cardiac output, with resultant increase in left atrial pressure and left ventricular filling pressure. Not only can this decrease in blood flow lead to syncope, this increase in atrial pressure or ventricular filling pressure can also result in increased production of atrial natriuretic peptide (ANP) and B-type natriuretic peptide (BNP). ANP and BNP are potent atrial and venous vasodilators that can override carotid and aortic baroreceptor reflexes attempting to compensate for decreased blood pressure. Patients with pacemaker syndrome exhibit increased plasma levels of ANP, and patients with so called atrial pressure "cannon a waves" (cause by atrial contraction against a closed valve) have higher plasma levels of ANP than those without "cannon a waves."

Natriuretic Peptides (ANP and BNP)

Atrial natriuretic peptide (ANP) is a hormone that is released from myocardial cells in the atria and in some cases the ventricles in response to volume expansion and increased wall stress. Brain natriuretic peptide (BNP) is a natriuretic hormone that is similar to ANP. It was initially identified in the brain but is also present in the heart, particularly the ventricles.

The release of both ANP and BNP is increased in heart failure (CHF), as ventricular muscle cells are recruited to secrete both ANP and BNP in response to the high ventricular filling pressures. The blood plasma concentrations of both hormones are increased in patients with asymptomatic and symptomatic left ventricular dysfunction, permitting their use in diagnosis. A Johnson and Johnson Company, Scios sells a popular intravenous (IV) medication Natrecor (nesiritide), a recombinant form of the endogenous human peptide for the treatment of decompensated CHF. The advent of Natrecor marked an important evolution in the understanding and treatment of acute heart failure.

Both ANP and BNP have diuretic, natriuretic, and hypotensive effects. They also inhibit the renin-angiotensin system, endothelin secretion, and systemic and renal sympathetic activity. Among patients with CHF, increased secretion of ANP and BNP may partially counteract the effects of norepinephrine, endothelin, and angiotensin II, limiting the degree of vasoconstriction and sodium retention. BNP may also protect against collagen accumulation and the pathologic remodeling that contributes to progressive CHF.

It is well established in scientific literature that infusion of ANP benefits patients with hypertension. Unfortunately, until now this knowledge had no practical applications since, due to its biochemical nature, ANP cannot be produced in a form of oral medication (a pill). There is therefore a need to develop novel ways to deliver ANP to patients who can benefit from it. Inventors propose to stimulate heart atria with an artificial implanted device to cause increased secretion of endogenous ANP.

SUMMARY

The inventors identified in this application observed that—while clearly deleterious to the majority of heart disease patients—the phenomenon of the reduction of blood pressure in response to nonphysiologic pacing can be beneficial by reducing blood pressure in the group of patients with severe hypertension and particularly ones with malignant drug refractory hypertension that frequently results in strokes and sudden death.

The inventors disclosed in co-pending applications a pacemaker that is counterintuitively used dissynchronously to generate different atrial and ventricular contraction rates. Specifically, a higher rate of atrial contractions than ventricular contractions is generated. It is understood that this may result in suboptimal performance of the heart. However, the inventors propose that this disadvantage of lower blood pressure from the reflex vasodilation and ANP secretion caused by nonphysiologic pacing can paradoxically benefit some hypertensive and heart failure patients if the increased ANP-BNP secretion from increased atrial pressures sufficiently increases the release of ANP and BNP hormones to a level that overcomes potential detriments from reduced atrial contribution to cardiac output.

One Embodiment, AV Blocked Electric Stimulation of the Heart

One embodiment disclosed here uses a modified implanted electronic cardiac pacemaker to increase ANP and BNP secretion by pacing the right atrium of the patient at an appropriately high rate. In the first described embodiment, patients have either a natural atrioventricular block (AV block) or have an AV block induced by heart tissue ablation or some other appropriate procedure. For example in patients with a so-called third-degree AV block (complete AV block, no AV conduction), no atrial impulses reach the ventricles, and ventricular rhythm is maintained by a subsidiary natural pacemaker. Since subsidiary pacemakers must be below the level of block, their location is in part determined by the site of block. In third-degree AV nodal block, the ventricular rhythm is usually maintained by pacemakers in the AV junction with resultant narrow QRS complexes. In third-degree AV block localized to the bundle branches, ventricular rhythm is maintained by a pacemaker in the Purkinje fibers, with resultant wide QRS complexes. The junctional pacemaker rate is usually faster (40-80 beats/min) compared with the peripheral Purkinje network (20-40 beats/min). In such patients, a dual chamber pacemaker can be used to pace atria at a rate much higher than the ventricles without the risk of patient developing dangerous ventricular tachycardia (rapid heart beat) as the atrial impulses, either native or pacemaker-induced, are not conducted to the ventricle. An atrioventricular (AV) node ablation is a known medical procedure that destroys a part of the heart's normal electrical system. The combination of pacing and AV node ablation is sometimes used clinically in patients with chronic atrial fibrillation and rapid ventricular response that poorly respond to drug therapy.

This is accomplished by cauterizing the AV node, which is located between the upper heart chamber (atria) and the lower heart chambers (ventricles). Once the AV node is cauterized, none or few impulses from the atria will be able to reach the ventricles. Currently, an AV node ablation is performed when the patient's rhythm disturbance (arrhythmia) originates in the atria and its effects on atrial or ventricular function cannot be controlled adequately with other measures. A permanent pacemaker is installed afterwards, to keep the heart beating at a normal rate. In this case, at least one pacemaker lead is connected directly to a ventricle.

Another Embodiment, Refractory Period Electric Stimulation of the Heart

Inventors realized that it is desired to implement nonphysiologic pacing with the purpose of increasing atrial wall stress and cause hormonal release and vasodilation without blocking natural AV conduction. Inventors discovered that such pacing modality is possible utilizing naturally occurring periods in the electric cyclic activity of the heart when the heart muscle conduction is blocked by so called refractory periods.

In the heart are specialized tissue collections that have a unique property, they rhythmically emit electrical impulses. The cause of these phenomena is the "leaky membrane that allows the regular exchange of Sodium, Potassium, and Calcium ions and causes a change in the polarization of the cells. Sodium ions move into the cell and start the depolarization, Calcium ions extend that depolarization. When the Calcium ions stop entering the cell Potassium ions move in and the repolarization of the cell begins. To simplify this, the Sodium starts the cells stimulation, the Calcium extends that stimulation to allow the entire muscle to contract before Potassium comes along and tells it to relax for a moment and get ready for the next wave. A material aspect of the repolarization depolarization cycle of the individual heart muscle elements is the "refractory" period where the cells reset for the next wave and temporarily cannot be electrically stimulated to contract or conduct.

These atrial, AV node and ventricular refractory periods have two stages, the Absolute and Relative refractory periods. In the Absolute refractory phase, the conduction system and heart muscle are in a "drained" state and need a moment to "recharge" to be able to electrically and/or mechanically respond to another electrical stimulus. Thus, a pacemaker impulse applied to these structure during this time would not be electrically conducted or cause the heart muscle to contract. In the relative refractory period that follows the absolute refractory period, the electrical conducting tissues and/or heart muscle cells are not fully "recharged" but may conduct and/or contract if excited with a strong pacing signal.

The refractory period of the atria in the naturally beating heart begins and ends before the end of the absolute refractory period of the ventricle. Therefore, it is possible to generate an electrical stimulus to pace the atria of the heart during the ventricular refractory period and generate the atrial contraction in such way that this electrical stimulus will not propagate through the AV node to the ventricle and cause a ventricular contraction.

To maximize the affect of the atrial contraction in the terms of maximum atrial muscle wall stress and the subsequent neural activation and hormonal release, it is desired to cause a contraction of the atrium when the atrium is filled with blood and its walls are distended. It is also desired to cause atrial contraction against the closed AV valve, causing the phenomenon somewhat similar to the pacemaker syndrome. This maximum stress in the atrial wall caused by the atrial contraction can be expected to result in the maximum vasodilatation of peripheral blood vessels that will achieve the desired reduction of systemic atrial blood pressure.

The atria of the heart naturally contract during the approximately 100 ms following the P-wave of the surface ECG of the heart. It is understood that for an implanted pacemaker internal electrograms from different heart chambers are available. It is therefore understood that references to surface ECG in regard to heart cycle timing are made for illustration and the corresponding electrical events can be easily detected using standard atrial and ventricular electrograms. The Q-wave of the surface ECG corresponds to the beginning of the absolute refractory period of the atria. The atria passively fill with blood during the ventricular systole, which occurs following the Q-wave of the surface ECG.

Approximately half-way or between 100 to 150 ms into the ventricular systole period, the atria are fully expanded and primed with blood and the window of opportunity for the maximum benefit from nonphysiologic atrial pacing begins. The ventricles contract during the ventricular systole of the heart and are absolutely refractory to electric stimulation during this period. Importantly, the atrial refractory period ends before the 50% of the ventricular systole has elapsed. The atria are now electrically and mechanically "armed" and can be triggered to contract by a pacing impulse. This window of opportunity can be defined as occurring from the end of the atrial refractory period (approximately 30 to 50% into the ventricular systole following the Q wave) and the end of the ventricular refractory period that corresponds to the middle of the T-wave, which is also the time when the aortic valve opens. During this time window, it is possible to apply a pacing signal to the atrium of the heart, generate a nonphysiologic atrial contraction without provoking the undesired nonphysiologic ventricular contraction. The timing diagram on the FIG. 5 of this application illustrates the principal of nonphysiologic atrial contraction.

In summary, the following exemplary novel algorithm has been developed to allow a pacemaker stimulated atrial contraction in an intact naturally beating heart:

A. The end of atrial refractory period is detected or predicted, based on physiologic monitoring of the heart, for example by detecting suitable event points of the patient's surface ECG or intracardiac atrial and ventricular electrograms. The end of atrial refractory period also corresponds to the end of the depolarization and mechanical contractile activity of the atrial heart muscle.

B. The atrium is paced to contract following the end of the refractory period of the atrium but before the end of the refractory period of the ventricle, for example in the middle of ventricular systole.

C. In one proposed embodiment, the resulting contraction of the atrium occurs in the later part of the ventricular systole when atrium is distended by passive filling with blood. A non-physiological, paced atrium contraction is then caused during this period which causes the atrium to contract against the closed AV valve, increasing atrial pressure and wall stress leading to beneficial neural and hormonal stimuli. These stimuli are expected to result in 1) peripheral vasodilatation and reduction of blood pressure in hypertensive patients or 2) increased ANP/BNP secretion leading to beneficial physiological and clinical sequelae in patients with CHF.

In one embodiment, a sensing and pacing lead of a pacemaker (implantable or temporary) is placed in an atrium (such as RA) of the heart. The intracardiac ECG (electrogram) is sensed for signs of atrial and ventricular depolarization and repolarization. The beginning and end of the atrial refractory period is predicted following a known delay after the P wave or R wave of the heart. For example, the atrium can be paced 150 milliseconds (ms) after the detected R wave. The desired delay can be recalculated by the embedded software based on the heart rate or set by the physician during the office visit of the patient. All modern pacemakers include suitable sensing, programmability and telemetry functions.

It is understood that there are many ways to detect various phases of the electric heart activity cycle using surface or intracardiac ECG, pressures, wall motion or heart sound sensors. It is imagined that some of these signals can be used to synchronize the proposed nonphysiologic pacing to the desired window of the heart cycle. Common to all of these potential embodiments, the heart atrium (right or left or both) is paced after the end of the atrial refractory period and before the end of the ventricular refractory period.

In this embodiment, a pacemaker is counter intuitively used dissynchronously to generate different atrial and ventricular contraction rates. Specifically, a higher rate of atrial contractions than ventricular contractions is generated. It is understood that this may result in suboptimal performance of the heart. The inventors propose that this disadvantage will be offset by the benefit of the increased beneficial vasodilatory stimulus and hormonal secretion by the heart atria in hypertensive and heart failure patients.

Electronic pacemakers are currently used to replace or supplement the natural pacing nodes of the heart by applying electric excitory signals to the heart muscle to cause contraction and blood pumping cycle. Pacemakers are used in patients with diseased nodes (slow heart beat) and defective (blocked) conduction pathways. Bi-ventricular pacemakers pace both ventricles of the heart to restore synchrony between the ventricles.

Generally, the conventional wisdom of all pacing therapies for the heart disease is as follows. A human heart consists of four chambers—two atria and two ventricles. In order for the heart to efficiently perform its function as a pump, the atrial muscles and ventricular muscles should contract in a proper sequence and in a timed relationship, as they do in a healthy heart. Therefore electronic pacemakers are used to restore the normal heartbeat or to restore synchrony between different chambers of the heart. It is understood that the methods and embodiments described in this patent may be incorporated into existing pacemaker devices, such as the pacemakers, biventricular pacemakers, or ICDs.

SUMMARY OF THE DRAWINGS

A preferred embodiment and best mode of the invention is illustrated in the attached drawings that are described as follows:

FIG. 4 illustrates intermittent asynchronous pacing.

DETAILED DESCRIPTION

Figure 1:
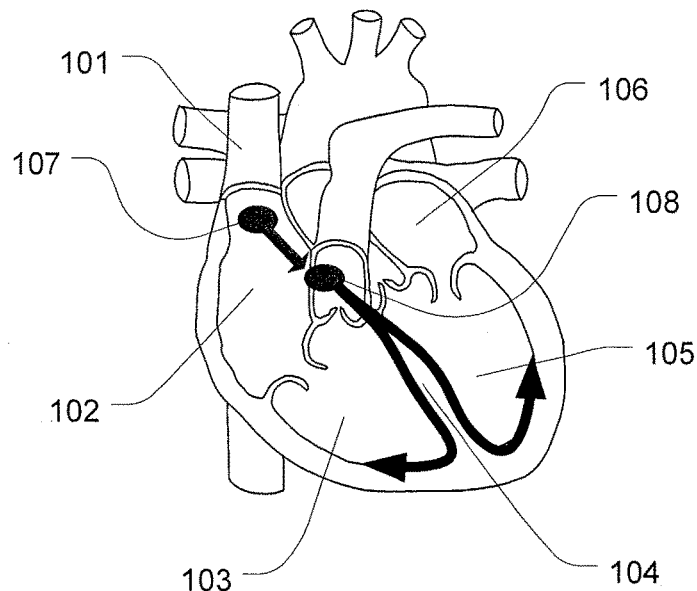
FIG. 1 illustrates the electric excitory pathways and chambers of a human heart.

FIG. 1 shows a normal heart. Electrical pulses in the heart are controlled by special groups of cells called nodes. The rhythm of the heart is normally determined by a pacemaker site called the sinoatrial (SA) node 107 located in the posterior wall of the right atrium 102 near the superior vena cava (SVC) 101. The SA node consists of specialized cells that undergo spontaneous generation of action potentials at a rate of 100-110 action potentials ("beats") per minute. This intrinsic rhythm is strongly influenced by autonomic nerves, with the vagus nerve being dominant over sympathetic influences at rest. This "vagal tone" brings the resting heart rate down to 60-80 beats/minute in a healthy person. Sinus rates below this range are termed sinus bradycardia and sinus rates above this range are termed sinus tachycardia.

The sinus rhythm normally controls both atrial and ventricular rhythm. Action potentials generated by the SA 107 node spread throughout the atria, depolarizing this tissue and causing right atrial 102 and left atrial 106 contractions. The impulse then travels into the ventricles via the atrioventricular node (AV node) 108. Specialized conduction pathways that follow the ventricular septum 104 within the ventricles rapidly conduct the wave of depolarization throughout the right 103 and left 105 ventricles to elicit the ventricular contraction. Therefore, normal cardiac rhythm is controlled by the pacemaker activity of the SA node and the delay in the AV node. Abnormal cardiac rhythms may occur when the SA node fails to function normally, when other pacemaker sites (e.g., ectopic pacemakers) trigger depolarization, or when normal conduction pathways are not followed.

Figure 2:
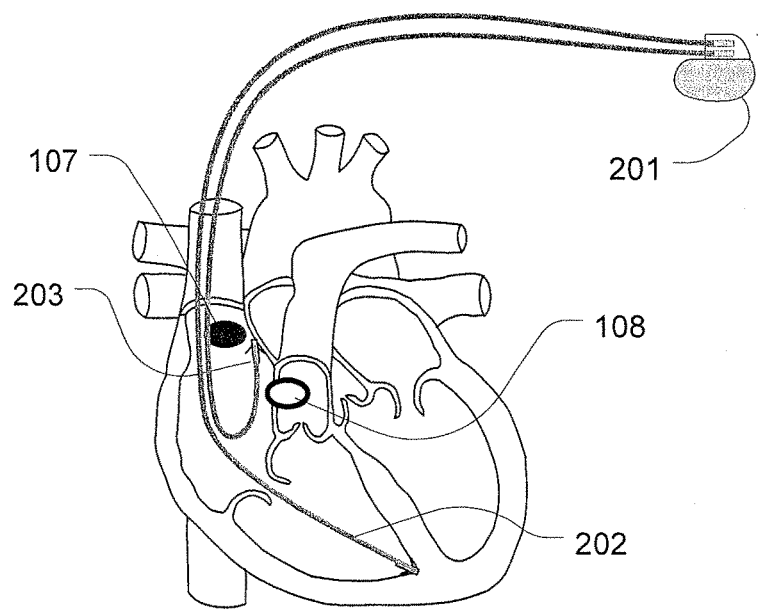
FIG. 2 illustrates an embodiment having a two lead pacing system.

FIG. 2 shows a heart treated with one embodiment. Pulse generator (pacemaker) 201 is implanted in a tissue pocket in the patient's chest under the skin. In this embodiment the generator 201 is connected to the heart muscle by two electrode leads. The ventricular lead 202 is in contact with the excitable heart tissue of the right ventricle 103. The atrial lead 203 is in contact with the excitable heart tissue of the right atrium 102. It is understood that the pacemaker can have more leads such as a third lead to pace the left ventricle 105. It is expected that in future cardiac pacemakers will have even more leads connecting them to various parts of the anatomy.

Leads 203 and 202 can combine sensing and pacing electrodes as known and common in the field. The atrial lead 203 can therefore sense the natural intrinsic contractions of the atria before they occur and communicate them to the generator 201. Atrial lead can be also used to implement backup pacing if the natural heart rate drops below the desired value (for example 50/min) as a result of the therapy. Similarly, ventricular lead 202 can be used for further backup ventricular pacing if atrial pacing was, for some reason, ineffective.

Ventricular lead 202 can be used to sense ventricular depolarization. This is significant since it allows accurate detection of the ventricular contraction when ventricle is refractory and A-V valve is closed. It also can be used to confirm that the therapeutic atrial pacing did not conduct to the ventricle. If conduction to atrium is detected, the timing of atrial pacing can be adjusted based on ventricular electrogram feedback.

Although it is possible to implement the embodiments disclosed herein using atrial lead only, ventricular lead adds to the reliability and safety of the proposed embodiment. The generator is equipped with the programmable logic that enables it to sense signals from leads and other sensors, such as motion or physiologic activity sensors, process the information, execute algorithms, and send out electric signals to the leads.

In one described embodiment the natural conduction path between the SA node 107 and the AV node 108 is blocked. The patient may already have a natural complete AV block. In this case no intervention is needed. If the patient has functional electric pathways from atria to ventricles, the patient's AV node can be disabled (blocked) by tissue ablation. It is understood that many irreversible and reversible methods of selectively blocking conduction in the heart are known. These include treatment with chemical agents and blocking with subthreshold electric stimulation (non-excitatory stimulation that does not cause muscle fibers to contract). Ablation of the AV node is used as an example since it is widely accepted and easily performed using RF energy catheters. Other devices that use cold, laser and ultrasound energy to perform ablation are also known.

Figure 3:
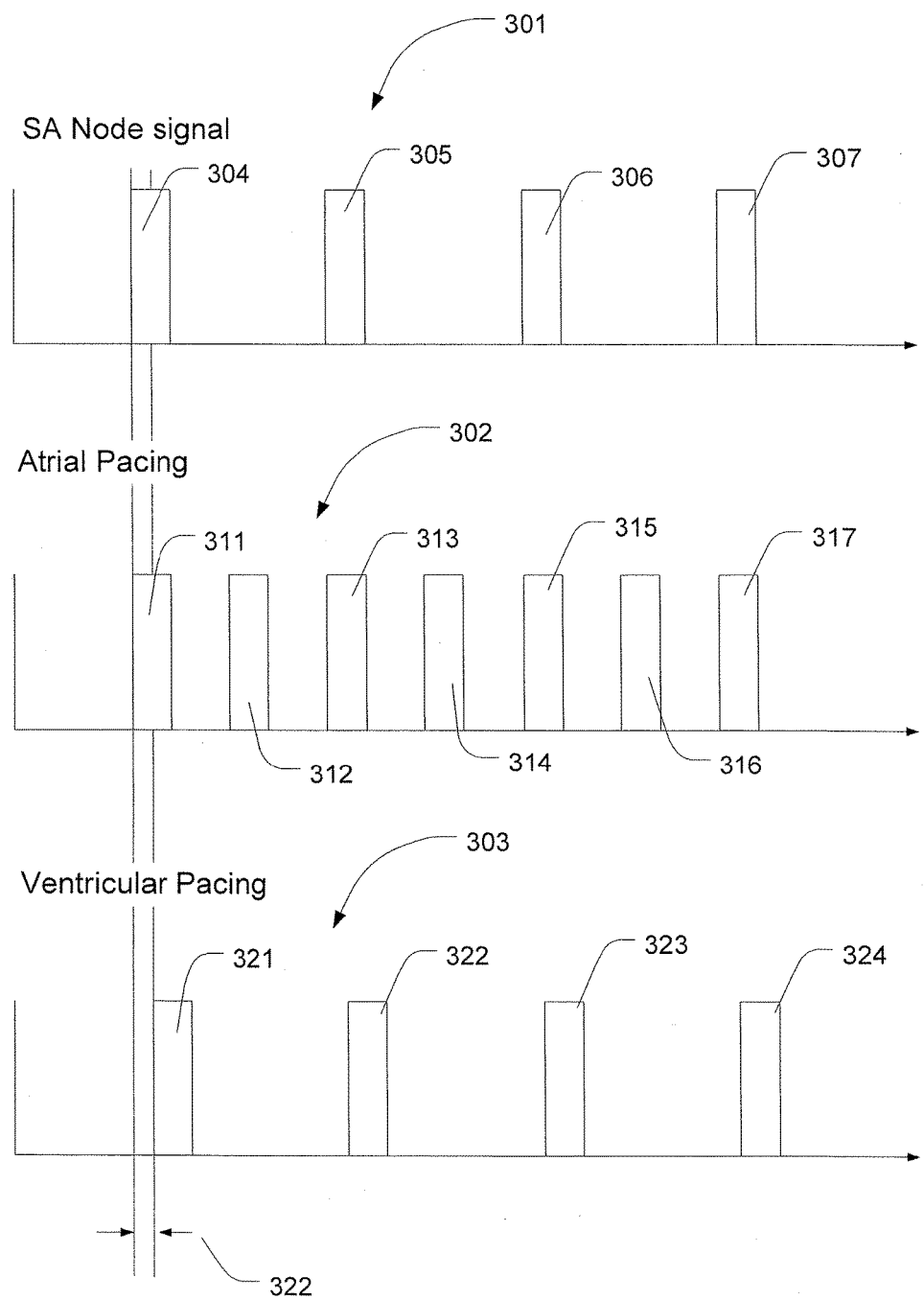
FIG. 3 illustrates one sequence of natural and induced stimulation pulses.

FIG. 3 illustrates sensing and pacing sequences for an embodiment having sequence of stimulation pulses. Pulses are simplified and presented as rectangular blocks spaced in time as represented by the X-axis.

Trace 301 illustrates the natural or intrinsic rate generated by the SA node of the heart. The SA node generates atrial polarization pulses 304, 305, 306 and 307. These pulses can be sensed by the atrial lead 203.

In response to the sensing of intrinsic atrial pulses, the pulse generator 201 generates a series of pulses represented by the trace 302. Pulses are conducted to the atria by the atrial lead 203. Device generated atrial stimulation pulses 311, 313, 315 and 317 are not needed if SA node generated atrial pulses 304, 305, 306 and 307 occur at desired rate, for example every second or faster. Ventricular pulses corresponding to naturally occurring atrial pulses 304, 305, 306 and 307 represent the intrinsic pumping heart rate. The generator 201 (based on an embedded algorithm) also generates extra atrial pulses 312, 314 and 316. Together natural pulses 304, 305, 306 and 307 or pacemaker generated pulses 311, 313, 315, 317 and asynchronous pulses 312, 314, 316 determine the atrial rate of the heart. Pacemaker pulses 311, 313, 315 and 317 represent atrial backup rate. They are only needed if native atrial pulses 304, 305, 306 and 307 do not occur in time to maintain the desired pumping heart rate.

Trace 303 represents ventricular stimulation pulses 321, 322, 323 and 324 conducted to the ventricle of the heart by the ventricular lead 202. The AV node of the heart in this embodiment is blocked during the entire heart cycle. Therefore the ventricular stimulation is always generated by the generator 201 based on an embedded algorithm. To ensure better performance of the heart ventricular pulses 321, 322, 323 and 324 are synchronized to the synchronous paced atrial pulses 311, 313, 315 and 317 or sensed atrial events 304, 305, 306 and 307 with a short delay 308 determined by the embedded algorithm that simulates the natural delay of the AV node conduction. Therefore for pumping heart beats, normal synchrony is maintained.

The algorithm illustrated by the FIG. 3 can be described as a sequence as follows:

a. sensing an intrinsic SA node generated atrial pulse (P-wave), b. generating a backup synchronous atrial pacing pulse if intrinsic atrial pulse is not sensed in time, c. calculating the intrinsic atrial rate based on previous SA node pulse intervals or pacemaker setting by programming and embedded logic, d. generating synchronous ventricular pacing signal delayed from the synchronous atrial pacing signal at the ventricular rate equal to the intrinsic SA node excitation rate (sinus rhythm), d. calculating the desired increased atrial rate, such as for example, a 2:1 (A:V) rate, e. generating asynchronous atrial pacing signal based on the calculated increased atrial rate, and f. waiting for the next intrinsic SA node generated atrial pulse (P-wave).

It is understood that this example of an algorithm is an illustration and many other embodiments of the algorithms can be proposed. It can be envisioned that more than 2:1 (atrial:ventricular) rate can be tolerated by the patient or that less than 2:1 rate is desired such as accelerating every second atrial beat.

In some clinical cases it may be not essential to preserve the natural sinus rhythm (from the SA node) when possible. In some patients it may be desired for the algorithm to take over the heart rate and force all the atrial contractions. Pacing modalities that do not rely on the SA node to generate the heart rate are known and used to treat bradycardia. The SA node of a patient can be ablated similar to the AV node and the embedded pacemaker algorithm will pace the atria. Alternatively, atria may be paced if the natural SA node pulse is not senses within the expected time from the last ventricular contraction. Various activity sensors such as accelerometers can be used to accelerate the heart rate as needed.

FIG. 4 illustrates an intermittent application of the proposed therapy. It is possible that some patients will not need or will not be able to tolerate continuous asynchronous A-V (atria-ventricular) pacing. In such patient period of normal (synchronous) pacing 401 is followed by the period of asynchronous (accelerated atrial) pacing 402 followed again by the period of synchronous pacing 403. The ventricular pacing rate 405 in this example stays the same. Switching between rates can be based on timing, patient's activity, or physiologic feedbacks. For example, the pattern of therapy using electrical stimuli to generate high atrial rates can be intermittent of varying duration of accelerated atrial pacing in intervals of 10-minute durations occurring, for example, 3 times per day. Alternatively asynchronous pacing periods 402 can be automatically, repeatedly and selectively applied when patient is at rest (for example as detected by a pacemaker motion sensor) or asleep.

Commonly, in comparison to previous devices, this embodiment purposefully creates ratios of atrial to ventricular contraction higher than 1:1, such as for example in the range of 1:1 to 4:1. In addition, any previous device that allowed more that a 1:1 ratio of contraction based this relationship on sensing native atrial depolarization and deferring generation of a ventricular pacing stimulus (skipping premature ventricular beats). In contrast, in the illustrated embodiment, the higher than 1:1 rate is intentionally and controllably initiated by the implantable generator. As a result the atrial rate is increased to a rate which causes the release of sufficient endogenous naturetic hormone to result in a therapeutically beneficial increase in blood plasma levels of the hormones or increased levels in any other vascular or non-vascular space in which these hormones a found.

It is desirable to cause a therapeutic increase of blood plasma ANP and BNP via an increased endogenous release of ANP and BNP from the atria of the patient's heart. Atrial release is mediated via increase of atrial wall stress. A preferred embodiment includes rapid pacing of the atria that is expected to increase the rate of contractions of the atria and release ANP and BNP. The embodiment has been described in connection with the best mode now known to the applicant inventors.

Figure 5:
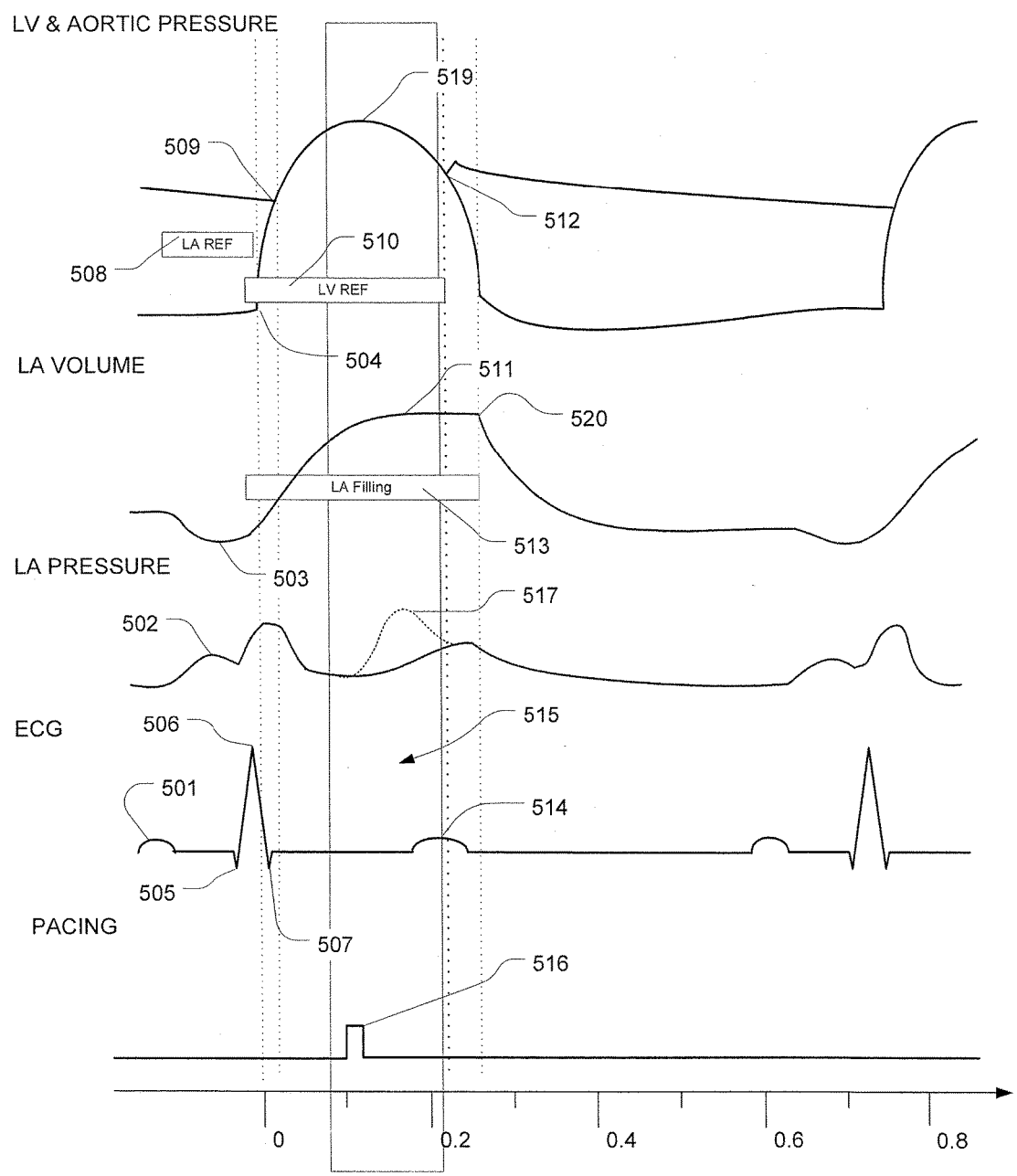
FIG. 5 illustrates timing of the refractory period pacing.

FIG. 5 illustrates the different, more sophisticated embodiment of the algorithm for refractory period atrial pacing of the heart. The heart (See FIG. 1) has intact electric conduction including substantially normal physiologic intact A-V node conduction delay. Pacing in this embodiment is implemented by electric stimulation with an atrial lead 203 (See FIG. 2). Sensing of electric activity can be performed with the atrial lead 203 or ventricular lead 202 or both. Although it is possible to infer all electric events in the heart needed to implement the therapy from atrial electrogram only, sensing both atrial and ventricular electric activity is likely to ensure the most reliable and precise operation of the device. When the patient ECG is discussed it is understood that the corresponding events can be reliably sensed in well known way by intracardiac leads.

Natural pacemaker or SA node of the heart initiates the Heart cycle with the P wave 501 of the ECG that corresponds to the atrial depolarization and the beginning of atrial contraction. It is also the beginning of the heart systole. Atrial pressure 502 increases and atrial volume 503 decreases. This time corresponds to the beginning of the atrial refractory period 508. During this period atria can not be paced to contract.

The P wave of the ECG is followed by the Q wave 505 that signifies the beginning of the isovolumic contraction of the ventricle. Ventricular pressure 504 rise begins rapidly. In response the Tricuspid and Mitral valves of the heart close. Ventricular refractory period 510 begins. At the end of isovolumic contraction 509 Pulmonary and Aortic valves open and the ejection of blood from the ventricle begins. Ventricular pressure reaches its peak in the middle of systole 519. Atrium is passively filled with blood as it relaxes 513. Approximately by the middle of systole both heart atria are filled with blood 511 and their refractory period is over. Atria are primed for a new contraction while the ventricle is ejecting blood. A-V valves are closed. At the same time the ventricle is still refractory and will not start another contraction in response to a natural or artificial pacing stimulus. Heart waves Q 505, R 506 and S 507 are commonly used markers of the beginning of the isovolumic contraction and the beginning of ventricular ejection (S wave). Modern pacemakers are equipped with means to read and analyze the electric activity of heart chambers that are suitable for this embodiment.

Systole ends when the aortic valve closes 512. Isovolumic relaxation of the ventricle starts. This point also corresponds to the middle of the T wave 514 of the ECG. The middle of T wave 514 corresponds to the end of the absolute refractory period of the ventricle. At the end of the T-wave Tricuspid and Mitral valves open and the atrium volume starts to drop 520 as the blood starts to flow from the atria into ventricles to prime them for the next ventricular contraction and ejection.

For this embodiment, the window of pacing opportunity 515 starts after the end of the atrial refractory period 508 and preferably but not exclusively after the atrium is filled with blood 511 and extended. During this window the atrium is primed and can be paced with a pacemaker pulse 516 that can occur at approximately the middle of systole or approximately 100-150 ms following the detected R wave 506. R wave can be sensed as ventricular polarization voltage by the ventricular lead 202 (See FIG. 2) It can also occur approximately 300 ms after P wave 501 is detected by the atrial lead. Both P-wave and R-wave can be used by themselves or in combination to trigger pacing 516. In response to pacing 516 atrium contracts generating a pressure rise 517 that results in the desired increased stress of the atrial wall muscle, release of atrial hormones and neurologic activation. Significantly the window 515 overlaps the ventricular refractory period 510. Pacing atria outside of that time period is not desired since it can cause an arrhythmia and a premature ventricular beat. It is anticipated that adjustments to timing will be needed if such pacing outside of the ventricular refractory period is detected as can be indicated by the presence of A-V conduction on electrograms (such as a Q wave follows a P wave).

As a result of the proposed therapy embodiment heart atria should beat at the rate 2:1 in relation to the heart ventricles. First physiologic atrial contraction 502 will be initiated by the natural pacemaker of the heart. Second non-physiologic atrial contraction 517 will occur during the heart systole, when the ventricle and/or AV node is refractory to stimulation. It may not be necessary to pace during every natural heart beat. Pacing can be applied only during part of the day or every second or third beat to give heart the needed rest and prevent of delay potential chronic dilation of the double-paced atria and potential heart failure.

Figure 6:
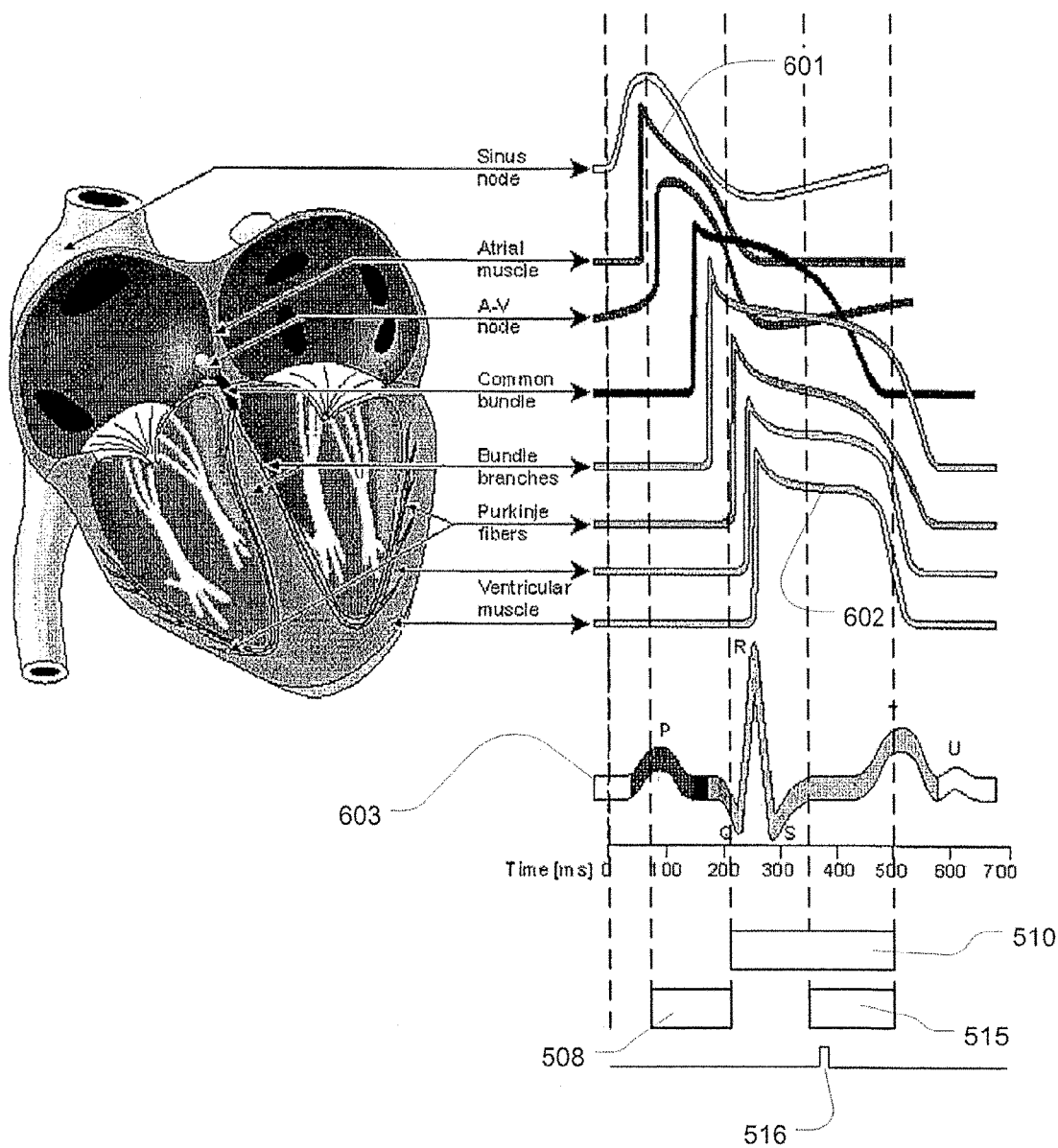
FIG. 6 illustrates an exemplary relationship between electric activity of the heart and an embodiment of a proposed pacing method.

FIG. 6 further illustrates a relationship between the electric activity of the heart and the proposed novel pacing method. Atrial refractory period corresponds to the depolarization of cells in the atrium muscle 601. Ventricular refractory period corresponds to the depolarization of cells in the muscle of the ventricle 510. Pacing 516 generates second atrial contraction during the window 515. Appropriate trigger points such as P-Q-R-S waves of the ECG 603 can be used by the embedded pacemaker software to generate the pacing spike 516 after an appropriate delay has elapsed from the selected P or R wave or both. This delay can be adjusted by the physician by reprogramming the pacemaker or automatically corrected based on the patient's heart rate and/or sensed level of physical activity. In most general terms pacing should occur after the R wave and before the T wave of the ECG 603. A delay of approximately 100-150 ms can be implemented after the R wave to allow atria to safely exit the relative refractory period and to allow atria to distend and fill with blood.

A preferred embodiment of the disclosed algorithm for a pacemaker stimulated atrial contraction in an intact naturally beating heart during ventricular refractory period may include the following additional steps:

A. Backup pacing to maintain pumping heart rate above certain value. This value can be constant or change based on physical activity.

B. Monitoring of physical activity to turn pacing on only when patient is at rest or adjusting pacing parameters based on activity.

C. Methods of automatically adjusting the timing of pacing. The goal of adjustments is to accommodate possible changes of the length of ventricular or AV node refractory period.

For the purpose of this disclosure ventricular refractory period relates the refractory state of the ventricle or the AV node for as long as the atrial natural or paced electric stimulation is blocked from propagating to the ventricle and causing a mechanical contraction of a ventricle.

In the embodiment disclosed herein, the therapy is implemented by an algorithm embedded in the implantable pacemaker that is equipped with an atrial lead and a ventricular lead. Both leads are equipped with electrodes capable of pacing appropriate chambers of the heart and sensing electric activity of these chambers, such as depolarization and action potentials.

It is a well known fact in the field of electrophysiology of the heart that if the heart's atrium is paced resulting in atrial contraction, the SA node (the natural pacemaker of the heart) becomes depolarized and the cyclical timing of the SA node becomes reset. This resetting of the SA node manifests as a delay of the next heartbeat originated by the next spontaneous SA node generated action potential. If the heart is beating naturally, following the periodic SA node cycling, inserting an AC means that the heart rate (HR) will be reduced.

When the heart rate or HR is discussed, it relates to the rate of ventricular contractions expressed in beats per minute (/min). It is sometimes called "pumping rate" for clarity. The time period separating two ventricular contractions (natural or paced) is called R-R interval and is expressed in milliseconds or ms. The HR is therefore equal to 60,000 ms divided by R-R interval.

It is understood that the HR can be reduced by the resetting of the SA node by the paced AC as described herein. It is also understood that the HR can be increased by atrial pacing or ventricular pacing at a rate that is faster than the native SA node rate or the reset (slowed down) SA node rate. Therefore the potentially excessive reduction of the HR by the invented method can be easily mitigated by backup pacing.

The aspects of the embodiments disclosed herein further are related to the effect of the proposed therapy on the heart rate. It is well recognized by cardiologists that appropriate reduction of the HR can be of some benefit to the patient in some cases. At the same time, if the HR becomes too low, below some individual level for the particular patient that can be determined clinically, the patient's blood pressure can become dangerously low. For example, a patient can be tested by a clinician prior to therapy. It could be found that the reduction of heart rate from 75 to 60/min was beneficial and tolerated, but the reduction of HR to or below 50/min resulted in hypotension. Parameters thus established can become programmed limits for the pacemaker logic. After the patient has lived with the pacemaker for some time, patient can be retested and the parameters can be adjusted. It is common to program and reprogram pacemakers using telemetry. The technology for programming exists and is well understood by pacemaker manufacturers and users. The specific programmable parameters of the proposed novel pacemaker logic are discussed below.

In the disclosed embodiments the AC is induced by the artificial atrial electric pacing pulse further called A2. A2 is issued by the pacemaker using the atrial lead after a delay, further called T1, and following a natural or paced atrial action potential further called A1. The A1 causes atrial contraction that is conducted to the ventricle and results in a ventricular contraction while A2 preferably does not unless it is intended to determine the length of ventricular refractory period. Different from A1 and to be effective, the A2 causes only atrial contraction that is not conducted to the ventricle. This is achieved primarily by the delay, further called T1, between A1 and A2 that is implemented by the pacemaker embedded electronics logic.

The pacemaker is also equipped with means to verify that the A1 and A2 events occur as desired. The most reliable method of verification is to acquire electrograms from both atrial and ventricular leads. Following an A1 there shall be a ventricular action potential, following an A2 there should be none. It is also possible to implement verification using only the atrial lead by sensing far field ventricular electric waves in the atrium. Such method of sensing ventricular electric signals in the atrium is known, but is considered less reliable. At the same time there is some advantage to having a pacemaker with only one atrial lead.

As we discussed above, to safely insert an AC as a part of long term chronic therapy, requires real-time monitoring and analysis of atrial and ventricular electrograms. In the medical practice it is expected that some patients will have abnormal electric conduction in the heart such as increased A-V delay, heart blocks of various degrees and premature atrial and ventricular contractions (PACs and PVCs). In addition to monitoring it is proposed to implement backup safety pacing to avoid risk.

As was disclosed previously there is a finite window of opportunity for AC insertion. Based on the experiments by inventors, it is likely more than 150-175 ms and less than or close to 300 ms on following the natural or paced atrial contraction A1 that propagated to the ventricle and generated a heartbeat. These limits, as well as the time needed for the SA node to recover, may vary from patient to patient and within the same patient depending on patient's activity, change of health, and other intrinsic and extrinsic factors. Therefore there is a need for embedded logic in the pacemaker that would have parameters settable by clinician and likely change the timing of pacing as needed based on physiologic feedbacks.

It is generally desired for the disclosed embodiments, to introduce paced AC towards the end, but not after the end, of the ventricular refractory period. Since the refractory period can change, method is proposed for dynamically adjusting the timing of pacing. In addition to passive adjustment based on continuous monitoring of atrial and ventricular electrograms active experiments can be automatically conducted by the embedded logic of the pacemaker. For the purpose of establishing the refractory period T1 can be gradually increased and decreased from heart beat to heart beat, by for example a 10 ms or other small time increment. Gradual increase of T1 will at some point result in the propagation of contraction from atrium to the ventricle, which can be detected. The embedded logic can use value T1 that is somewhat less (for example by 30 ms) than thus experimentally established ventricular refractory period. It can be envisioned that a skilled pacemaker designer can implement other real time algorithms to enable insertion of PACs at the time close to the end of the ventricular refractory period.

Figure 7:
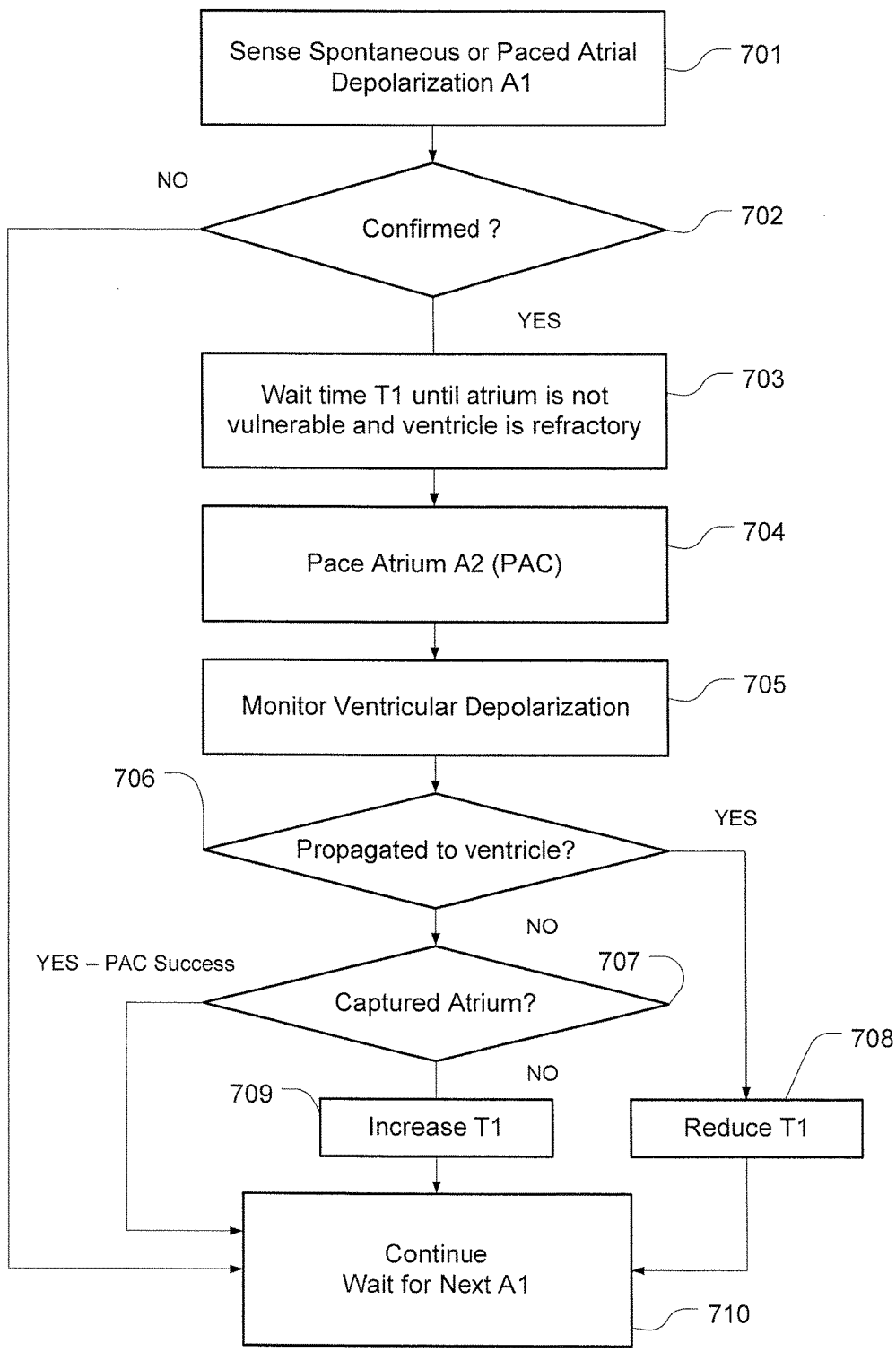
FIG. 7 illustrates an exemplary group of elements of an embodiment of embedded logic of a pacemaker.

FIG. 7 illustrates one group of elements of the embedded logic. Pacemaker logic senses 701 the A1 event that can be: spontaneous atrial action potential sensed by atrial lead, spontaneous ventricular action potential sensed by ventricular lead or a paced event applied by atrial or ventricular lead. For certainty, it can be envisioned that a combination of some of this events may be required to identify the event as a true A1 event. Confirmation of the true A1 event 702 can be required. For example, if a spontaneous atrial event is sensed, action can be delayed until the ventricular action potential is sensed, this confirming propagation. If the A1 event is a paced atrial event, confirmation of capture and ventricular contraction can be required to implement the rest of the therapy algorithm during the same (as sensing 701) heart cycle. Alternatively the logic may wait until the next A1 event 710.

An important parameter of the proposed therapy is the delay T1 703 that separates the sensed A1 event from the AC insertion event 704.

The proposed logic is designed to address issues associated with both too short and too long T1 delays. If the T1 delay is too short, there may be risk of inducing atrial fibrillation. There is also a functional limitation to the minimum T1. The atrial tissue is refractory for some amount of time and pacing during that absolute atrial refractory period will not cause capture of the atrium and conduction of pacing stimulus throughout the atrium and back to the SA node. In addition, while the SA node does not have a refractory period, there is a certain amount of time during which impulses originating in the atria will not enter the SA node. Thus, if logic paces too early after A1, the A2 pacing stimulus will not conduct back into the SA node and will not cause resetting of the SA node and the atrial contraction.

Logic validates the A2 event 706 by sensing propagation of the heart cycle from the atrium to the ventricular action potential with the ventricular lead. If the ventricular action potential propagation occurs 706 (indicating contraction) following A2, the delay is likely too long. Logic can reduce the delay 708 by some amount, for example 20 ms, before the next heart cycle.

Logic can also test that the electrically paced A2 event actually caused atrial contraction or "capture" 707. If capture did not occur and the atrium did not contract the delay T1 may need to be increased.

It is understood that the elements of logic presented by the FIG. 7 are relatively independent and can be selectively implemented in a pacemaker.

Figure 8:
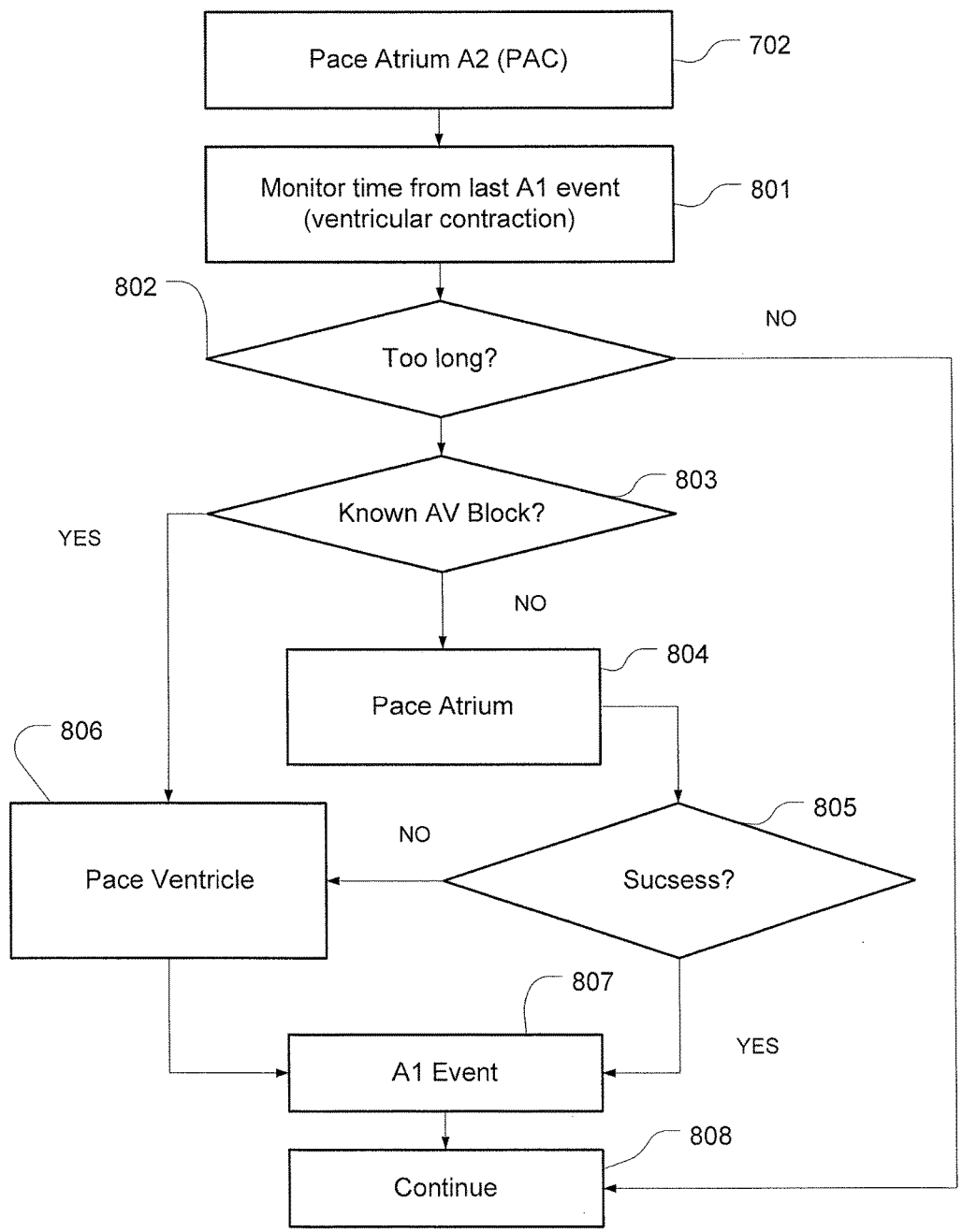
FIG. 8 illustrates an exemplary group of elements of an embodiment of embedded logic of a pacemaker, primarily related to protecting a patient from excessively low heart rate induced by therapy.

FIG. 8 illustrates another group of elements of the embedded logic primarily related to protecting the patient from excessively low heart rate induced by therapy.

Execution of this logic can start with the event of a confirmed AC 702 (See FIG. 7) that implies that the heart cycle is likely to be prolonged, but counting of the R-R interval 801 starts from the last confirmed ventricular contraction. For example, logic can start counting elapsed R-R interval time form last ventricular action potential sensed by the ventricular lead. It is anticipated that the programmability of the logic will allow clinician to set maximum allowed R-R interval for the patient. For example, setting of 1,000 ms will mean that the HR is not allowed to drop below 60/min without logic taking action. If the observed time exceeds the limit 802 logic forces a heartbeat to maintain blood pressure.

If next spontaneous atrial A1 event is not identified by the time allowed, atrium is paced and the A1 event is forced. If patient has a known A-V conduction block 803, ventricle can be paced instead 806. If the paced A1 event 804 did not result in the successful capture and ventricular contraction 805, ventricle can be paced. In any case the new A1 event is generated and the heart rate is maintained by all available means above the clinically acceptable minimum level. This level can be preset in the embedded logic or adjusted based on the patient's activity level.

Figure 9:
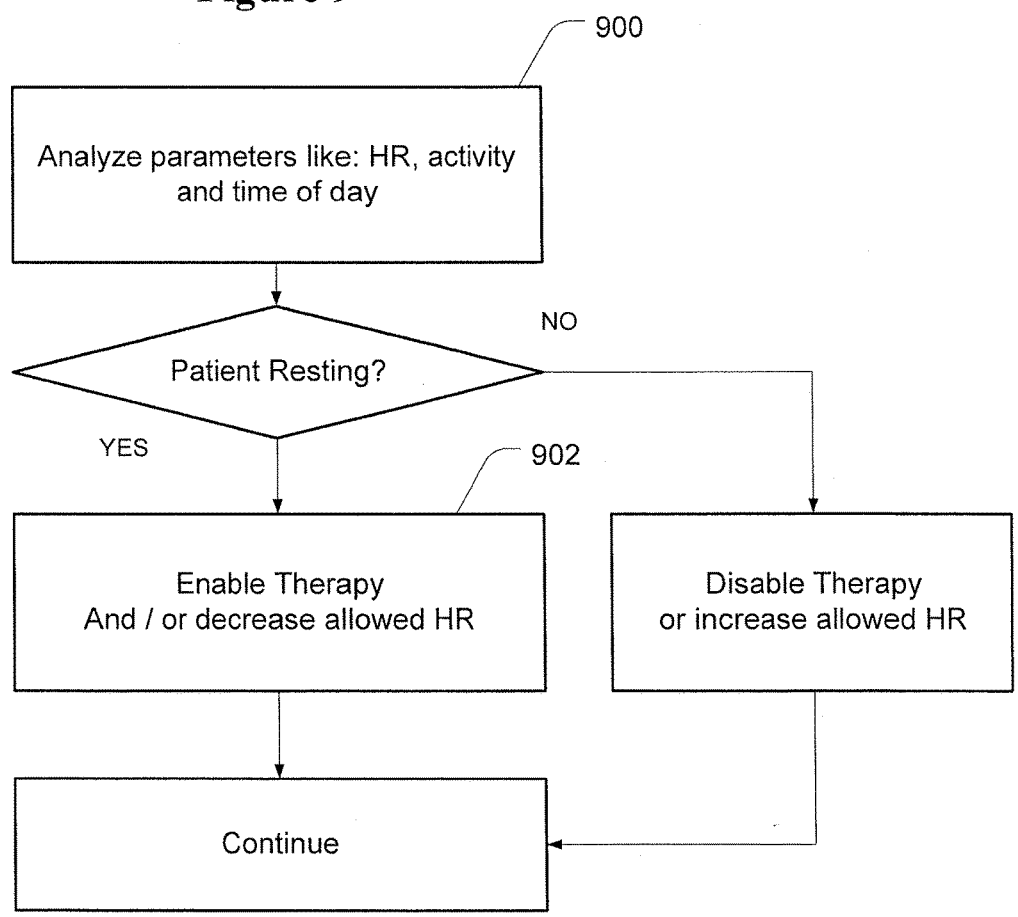
FIG. 9 illustrates an embodiment of logic for a more flexible, adaptive implementation of therapy.

FIG. 9 illustrates one embodiment of logic for a more flexible, adaptive implementation of the therapy. It is known that during exercise humans rely on increased HR to sustain blood pressure and oxygen delivery. It is desired that the pacemaker does not interfere with physical activity. Logic can rely on known methods such as accelerometers to detect motion to identify activity 900. In addition, patient's breathing can be sensed to automatically initiate and control pacing as needed. Embedded sensors such as transthoracic impedance measurement are used in pacemakers to monitor breathing. Slow, shallow regular breathing is an indication that the patient is at rest. Increase of respiration rate and depth indicates physical activity. Pacing may be applied when patient is asleep or at rest 901. Motion sensors such as accelerometers can be used to detect that the patient is resting. Almost all modern pacemakers include at least one activity sensor, typically an accelerometer. Alternatively the information can be derived from the respiration pattern and heart rhythm or a combination of these parameters to increase the certainty of detection. In another possible embodiment, patient may turn pacing on, when going to bed to sleep or rest and turn it off when awake or active. Patient may communicate to an implanted device using known methods such as magnets and magnetic sensors, RF communication and others. As an alternative to turning pacing on and off parameters that determine maximum and minimum allowed heart rate limits can be adjusted. Delay T1 can be reduced, when activity is detected and/or maximum allowed R-R interval can be made shorter. Other ways of adjusting pacing timing based on activity are known in the field of demand pacing.

Figure 10:
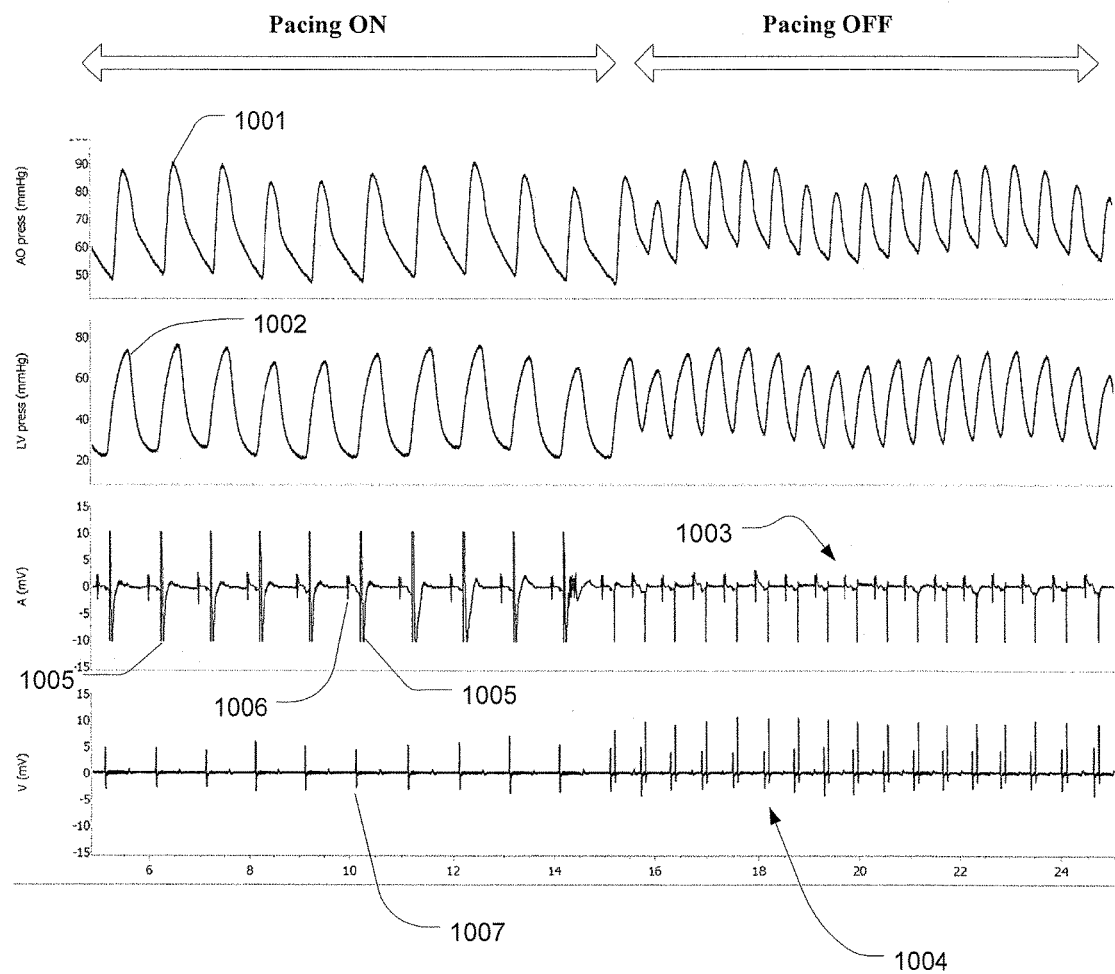
FIG. 10 illustrates traces from an experiment testing an embodiment of a pacing method.

FIG. 10 illustrates an experiment conducted by inventors to test the embodiment in an animal. Traces from the top are: Aortic Blood Pressure 1001, Left Ventricular Blood Pressure 1002, Atrial electrogram 1003 and Ventricular electrogram 1004. When pacing is ON (left panel) heart rate and blood pressure are reduced. Pacing is applied to the atrium and is indicated by large spikes 1005 on the atrial electrogram 1003. Pacing spike 1005 is delayed by 200 ms from natural atrial depolarization 1006 and by 80 ms from natural ventricular depolarization 1007. As desired, atrial pacing 1005 did not propagate to ventricular contraction as evidenced by the ventricular electrogram 1004 and left ventricular pressure trace 1002. Pacing 1005 generated an inserted AC as described in this application. When pacing is OFF heart rate is between 100-104 bpm. When pacing is ON heart rate varies between 60-64 bpm since it is determined by the intrinsic SA node activity.

Figure 11:
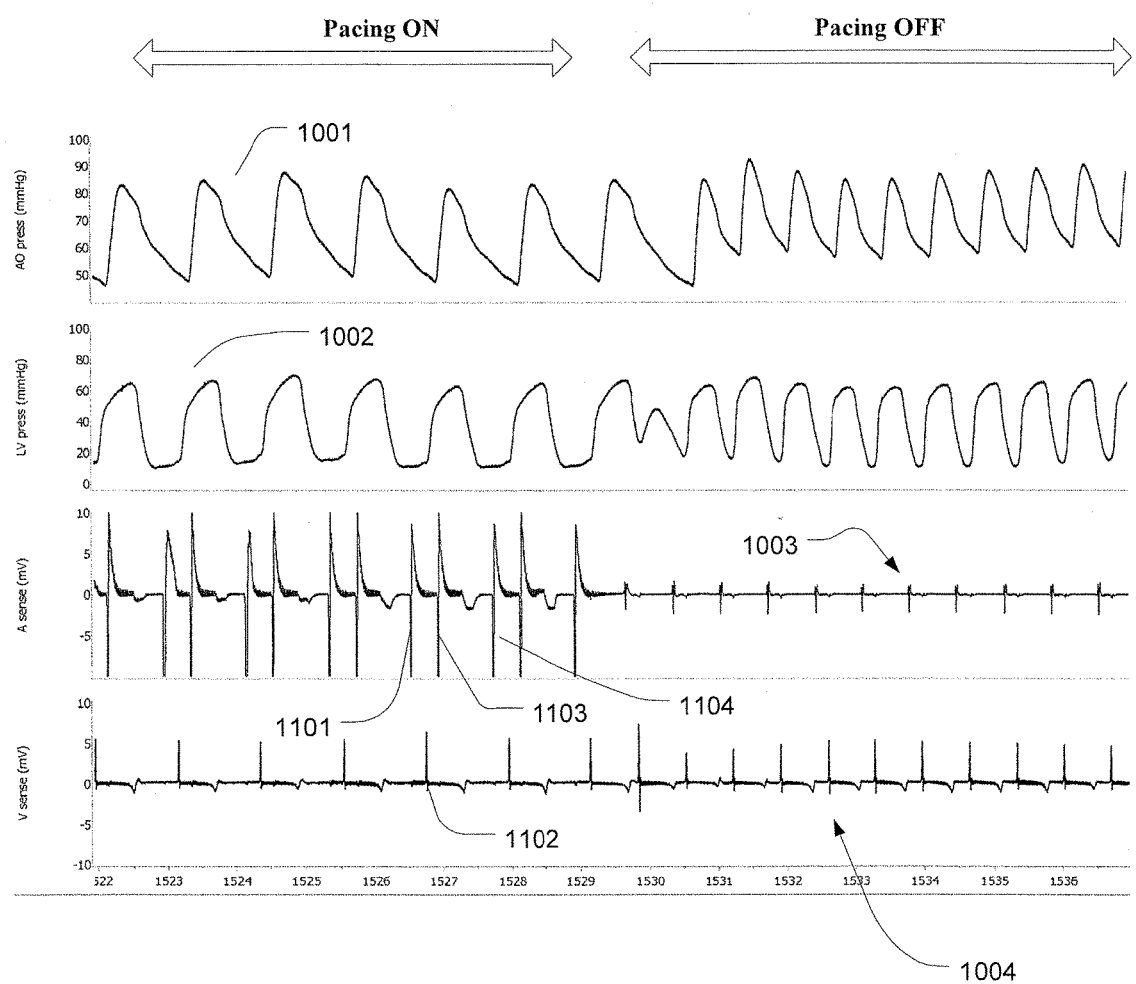
FIG. 11 illustrates traces from another experiment testing another embodiment of a pacing method.

FIG. 11 illustrates a different experiment conducted by inventors to test the embodiment in an animal to test implementation of backup pacing in addition to AC insertion. Traces from the top are the same as on the FIG. 10: Aortic Blood Pressure 1001, Left Ventricular Blood Pressure 1002, Atrial electrogram 1003 and Ventricular electrogram 1004.

Different to FIG. 10 two artificial pacing signals are applied per each heart beat. Backup pacing pulse 1001 is applied to the atrium outside of the refractory period. It propagates to the ventricle and causes ventricular depolarization 1102. Pacing pulse 1103 is applied during the refractory period of the ventricle and generates a AC. Pacing 1103 is delayed by 400 ms from backup pacing 1101 and by 200 ms from atrial depolarization 1103. It also results in the delay of the natural SA node rhythm and the next heartbeat is initiated by the next pacing spike 1004. When pacing is ON (Left Panel) heart rate is exactly 50 bpm and determined by backup pacing. When the pacing is turned OFF native heart rate is 80-84 bpm determined by the SA node activity.

FIG. 10 illustrates how in the setting of relatively fast intrinsic heart rate it could be safely reduced just by inserting an AC 200 ms after each atrial depolarization. FIG. 11 illustrates how in the setting of slower intrinsic heart rate backup pacing can be useful to maintain heart rate above minimum allowed value (50 bpm in this case). Both figures illustrate how both atrial and ventricular electrograms can be used to time pacing (by counting time delay after easily detectable atrial or ventricular depolarization spike). They also illustrate how the electrograms can be used to confirm propagation of pacing from the atrium to the ventricle.

A method has been developed of controllably reducing blood pressure in a human using an implantable cardiac pacemaker capable of pacing an atrium of a heart comprising: sensing the ventricular refractory period, pacing the atrium of the heart during ventricular refractory period, with a first pacing pulse, where said first atrial pacing pulse is blocked and does not propagate to the ventricle, where said first atrial pacing pulse further results in atrial contraction against a closed A-V valve and induced increased atrial wall stress resulting in ANP release by the stressed atrial wall; monitoring resulting HR of the patient; applying second pacing pulse to the atrium of the heart if the HR is less than minimum allowed HR value set by the pacemaker logic.

A method has been developed that controllably reduces blood pressure in a human using an implantable cardiac pacemaker capable of pacing an atrium of a heart comprising: sensing first ventricular contraction of the heart, pacing the atrium of the heart after a preset delay following said contraction, during ventricular refractory period, with a first pacing pulse, where said first atrial pacing pulse is blocked and does not propagate to the ventricle; monitoring resulting HR of the patient; and applying second pacing pulse to the atrium of the heart if the HR is less than minimum allowed HR value set by the pacemaker logic.

The method may further comprise steps of reducing said delay time if the said first atrial pacing is detected to propagate to the ventricle. The method may further comprise the steps of periodically increasing said delay to determine the end of ventricular refractory period. The method may further comprise setting the time of said second atrial pacing to a time slightly less than the determined refractory period. The method may further comprise suspending therapy if patient's exercise activity is detected by the pacemaker. The method may further comprise atrial pacing delivered in response to sensed ventricular depolarization. The method may further comprise atrial pacing delivered in response to sensed ventricular depolarization after a preset delay from said sensed ventricular depolarization. The method may further comprise atrial pacing delivered in response to sensed atrial depolarization. The method may further comprise suspending and restarting therapy based on the sensed patient's exercise activity as detected by the pacemaker.

A method has been developed of artificially inducing atrial wall stress to induce a peripheral vascular vasodilation and thereby effect a change in the blood pressure in a patient, the method comprising the steps of: detecting ventricular depolarization; applying atrial pacing to induce atrial contraction, where said pacing is applied when the ventricular pressure is higher than atrial pressure and when the AV conduction is refractory and said atrial pacing is blocked and does not propagate to the ventricle; monitoring resulting HR of the patient; and applying second backup pacing to the atrium or ventricle of the heart if the HR is less than minimum allowed HR value set by pacemaker.

A method has been developed of controllably reducing heart rate by pacing a heart of a patient having an atria and a ventricle comprising: sensing first ventricular contraction of the heart; pacing the atrium of the heart, where the atrial pacing occurs after the end of the atrial refractory period, during the ventricular refractory period of the heart and results in an atrial contraction that is not propagated to a second ventricular contraction, where said atrial contraction results in vasodilation and ANP release.

The method may further include a step of monitoring of the ventricular contraction resulting from pacing and adjusting the time of the said atrial pacing. The method may further include where said pacing occurs after a delay time following said sensed ventricular contraction. The delay may be adjusted based on the propagation of the said pacing to the ventricle. The method may further including a step of monitoring of a spontaneous heart beat after said pacing and delivering another pacing to the heart if the delay is longer than a preset time, where the preset time corresponds to a lowest selected heart rate and thus applied pacing generates ventricular contraction.

The invention has been described in connection with the best mode now known to the applicant inventors. The invention is not to be limited to the disclosed embodiment. Rather, the invention covers all of various modifications and equivalent arrangements included within the spirit and scope of the appended claims.

What is claimed is:

1. A method for controlling heart contraction to reduce blood pressure, the method comprising:
    allowing for a first atrial contraction of an atrium of a heart of a patient;
    allowing for a first ventricular contraction of a ventricle of the heart of the patient;
    pacing the heart during a pacing period after expiration of an atrial refractory period associated with the first atrial contraction and within a ventricular refractory period associated with the first ventricular contraction; and
    causing, by the pacing of the heart during the pacing period, a second atrial contraction without eliciting a corresponding second ventricular contraction.

2. The method of claim 1, wherein allowing for the first atrial contraction comprises one of sensing the first atrial contraction and pacing the first atrial contraction, and
    wherein allowing for the first ventricular contraction comprises one of sensing the first ventricular contraction and pacing the first ventricular contraction.

3. The method of claim 1, wherein the second atrial contraction causes a vasodilation and a release of natriuretic hormone.

4. The method of claim 1, wherein the second atrial contraction occurs when the atrium is distended with blood.

5. A method for treating a blood pressure disorder in a patient, the method comprising:
    pacing a heart of the patient so as to cause an atrial contraction against a closed heart valve;
    causing increased atrial wall stress by the atrial contraction;
    causing release of a natriuretic hormone by the increased atrial wall stress; and
    reducing the patient's blood pressure from a pretreatment blood pressure by the released natriuretic hormone.

6. A device for controlling heart rate by pacing a heart of a patient having an atrium and a ventricle, the device comprising:
    at least one electrically conductive lead configured to connect to the heart of the patient;
    an electrical pulse generator connectable to the at least one electrically conductive lead and configured to:
        pace, after a first ventricular contraction of the heart, the atrium of the heart, wherein the atrial pace occurs after expiration of an atrial refractory period of the heart and during a ventricular refractory period of the heart, and
        cause an atrial contraction as a result of the atrial pace, wherein the atrial contraction does not elicit a second ventricular contraction.

7. The device of claim 6, wherein the electrical pulse generator is configured to cause the atrial contraction when the atrium is distended with blood.

8. The device of claim 6, wherein the atrial contraction causes a vasodilation and a release of a natriuretic hormone in the heart.

9. The device of claim 8, wherein the electrical pulse generator is configured to monitor a ventricular contraction rate resulting from the atrial pace to determine whether the atrial pace conducts to the ventricle, and to adjust the atrial pace based on the monitoring.

10. The device of claim 8, wherein the electrical pulse generator is configured to pace the atrium upon expiration of a predetermined delay after the first ventricular contraction.

11. The device of claim 10, wherein the electrical pulse generator is configured to adjust the predetermined delay based on a detected propagation of the atrial pace to the ventricle.

12. The device of claim 10, wherein the predetermined delay is between approximately 150 milliseconds and 300 milliseconds after the first ventricular contraction.

13. The device of claim 8, wherein the electrical pulse generator is configured to monitor a spontaneous heart beat after the electrical pulse generator applies an atrial pacing pulse, and to deliver another atrial pacing pulse if a predetermined delay after the first ventricular contraction is longer than a predetermined period corresponding to a lowest selected heart rate, wherein the another atrial pacing pulse generates ventricular contraction.

14. The device of claim 13, wherein the lowest selected heart rate is less than approximately 50 beats per minute.

15. The device of claim 8, wherein the electrical pulse generator is configured to cause the atrial contraction in approximately a middle of ventricular systole.

16. The device of claim 8, wherein the electrical pulse generator is configured to cause the atrial contraction when an atrioventricular valve between the atrium and the ventricle is closed.

17. The device of claim 8, wherein the electrical pulse generator is configured to pace a right atrium, a left atrium, or both the left and right atria.

18. The device of claim 8, wherein during a given cardiac cycle a first atrial contraction occurs followed by the first ventricular contraction, and wherein, in being configured to cause the atrial contraction as a result of the atrial pace, the electrical pulse generator is configured to cause a second atrial contraction after the first atrial contraction and the first ventricular contraction.

* * * * *